United States Patent
Pelissier et al.

(10) Patent No.: US 11,915,820 B2
(45) Date of Patent: Feb. 27, 2024

(54) SYSTEMS AND METHODS FOR INITIATING CREATION OF A PATIENT ACCOUNT ON A MEDICAL IMAGING SYSTEM DURING A MEDICAL IMAGING EXAMINATION

(71) Applicant: Clarius Mobile Health Corp., Burnaby (CA)

(72) Inventors: Laurent Pelissier, North Vancouver (CA); Kris Dickie, Vancouver (CA); Trevor Stephen Hansen, North Vancouver (CA); Jacob Ruben Barrera Loredo, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 297 days.

(21) Appl. No.: 17/070,742

(22) Filed: Oct. 14, 2020

(65) Prior Publication Data
US 2022/0115116 A1    Apr. 14, 2022

(51) Int. Cl.
*G16H 10/60*    (2018.01)
*A61B 8/00*    (2006.01)
*G06F 16/51*    (2019.01)
*G06F 21/62*    (2013.01)
*G06Q 10/06*    (2023.01)
*G16B 20/20*    (2019.01)
*G16H 30/20*    (2018.01)
*G16H 40/20*    (2018.01)

(52) U.S. Cl.
CPC ............ *G16H 30/20* (2018.01); *A61B 8/465* (2013.01); *G06F 16/51* (2019.01); *G06F 21/6245* (2013.01); *G16H 40/20* (2018.01)

(58) Field of Classification Search
CPC ........ G16H 30/20; G16H 40/20; A61B 8/465; A61B 6/465; A61B 6/563; A61B 8/0866; A61B 8/565; G06F 16/51; G06F 21/6245; G06F 16/739; G06F 2221/2117; G06F 21/45
See application file for complete search history.

(56) References Cited

U.S. PATENT DOCUMENTS

| | | | |
|---|---|---|---|
| 2008/0263048 A1 * | 10/2008 | Wise ...................... | G06Q 10/10 707/999.009 |
| 2012/0303386 A1 | 11/2012 | Zavaleta et al. | |
| 2014/0278548 A1 | 9/2014 | Munro et al. | |
| 2016/0170636 A1 * | 6/2016 | Lee ....................... | G06F 3/0482 715/773 |
| 2020/0294640 A1 * | 9/2020 | Ginsburg ............... | G16H 40/20 |

* cited by examiner

*Primary Examiner* — Maroun P Kanaan
(74) *Attorney, Agent, or Firm* — Julian Ho; Susan Ben-Oliel

(57) ABSTRACT

The present embodiments relate generally to a system and method for creation of a patient account on a medical imaging system during a medical imaging examination. The method may involve operating a processor to: acquire a set of medical imaging data during the medical imaging examination, the set of medical imaging data being acquired in association with a logged-in medical professional account on the medical imaging system; display a new patient account prompt to initiate creation of the patient account; receive a patient identifier to initiate the creation of the patient account; and use the patient identifier to initiate the creation of the patient account, the patient account to be used for accessing at least a portion of the set of medical imaging data acquired during the medical imaging examination.

18 Claims, 19 Drawing Sheets

Welcome janedoe,

You are almost there! Let's verify your email so that you can log into the Clarius Cloud and App.

902

Thank you!
Team Clarius

© 2020 Clarius Mobile Health, all rights reserved.

Name your Act One™ Movie

Baby's First Movie!

Select a theme

Act One Bundle unlocked!

✓ Access to custom themes
✓ Download images/videos in HD

SYSTEMS AND METHODS FOR INITIATING CREATION OF A PATIENT ACCOUNT ON A MEDICAL IMAGING SYSTEM DURING A MEDICAL IMAGING EXAMINATION

FIELD

The present disclosure relates generally to medical imaging, and in particular, systems and methods for initiating creation of a patient account on a medical imaging system during a medical imaging examination.

BACKGROUND

Medical imaging examinations are medical procedures that involve generating visual representations of a patient's body in the form of images. The generated images may be used by medical professionals to evaluate the health or condition of the patient. For example, medical doctors may rely on the medical images to diagnose or treat disease. Medical imaging examinations may involve different types of imaging modalities, such as x-ray, magnetic resonance imaging (MRI), or ultrasound, for example.

The images generated during a medical imaging examination may be electronically stored or archived for future use. In particular, the images may be stored to form an electronic medical history for the patient. For example, the electronically stored images may be used to establish a baseline in order to identify changes in the patient during subsequent medical imaging examinations.

Patients may wish to access medical images subsequent to a medical imaging examination. For example, a patient may desire to receive a copy of a sonogram taken during a prenatal examination. However, providing patient access to electronically stored medical images may present certain security and privacy risks. Many jurisdictions have strict legislative or regulatory measures that protect the confidentiality of medical records, including medical images.

One potential method to provide secure patient access to electronic medical images is through the creation of user accounts. A user account associated with a patient (e.g., a patient account) can be used to authenticate the patient's identity and control their access. However, the process for creating a patient account is often lengthy and cumbersome for patients. A patient may not have sufficient time to create a patient account during a medical imaging examination. For example, a patient may need to provide a username, a password, contact information, as well as other personal information, in order to create a patient account. Also, after the medical imaging examination is completed, a patient may not be able to easily access the various information required to create the patient account, such as the medical professional, medical institution, and the like. This cumbersome process may dissuade patients from creating a patient account, despite their desire to access medical media.

There is thus a need for improved systems and methods for initiating creation of a patient account on a medical imaging system. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
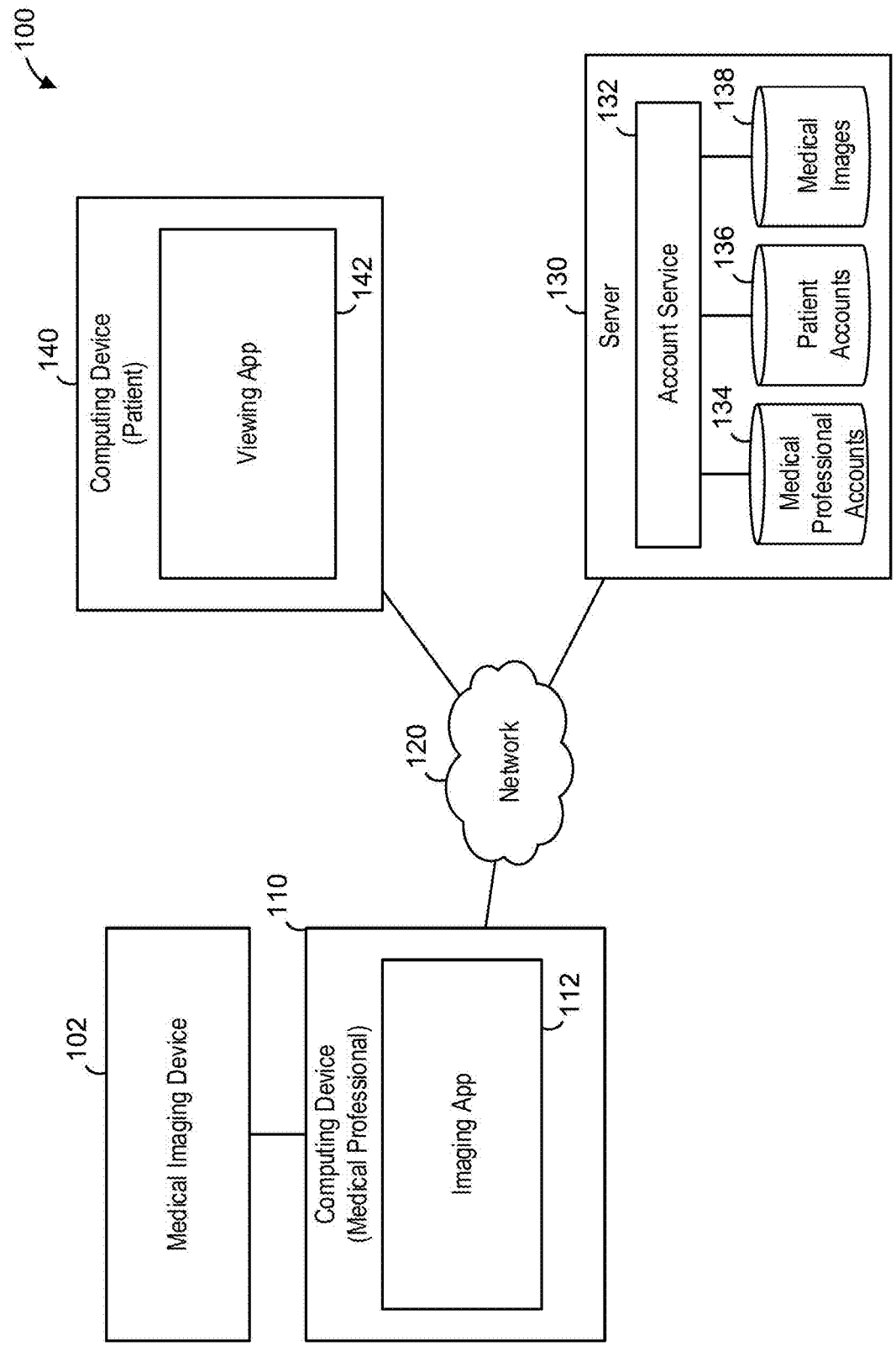
FIG. 1 shows a block diagram of an example medical imaging system, in accordance with at least one embodiment of the present invention.

In a broad aspect of the present disclosure, there is provided a method for initiating creation of a patient account on a medical imaging system during a medical imaging examination. The method involves operating a processor to: acquire a set of medical imaging data during the medical imaging examination, the set of medical imaging data being acquired in association with a logged-in medical professional account on the medical imaging system; display a new patient account prompt to initiate creation of the patient account; receive a patient identifier to initiate the creation of the patient account; and use the patient identifier to initiate the creation of the patient account, the patient account to be used for accessing at least a portion of the set of medical imaging data acquired during the medical imaging examination.

In some embodiments, the new patient account prompt may be displayed while the medical professional account remains logged in on the medical imaging system.

In some embodiments, using the patient identifier to initiate the creation of the patient account may involve operating the processor to: initiate the creation of the patient account as a subsidiary account of the medical professional account, the subsidiary account being assigned a lower access level to medical data accessible via the medical imaging system than an access level assigned to the medical professional account.

In some embodiments, the method may involve, after completion of the medical imaging examination, operating the processor to: use the patient identifier to request a patient access approval prior to granting access to the set of medical imaging data acquired during the medical imaging examination.

In some embodiments, the patient identifier may include a contact data and the method may involve operating the processor to, after the initiation of the creation of the patient account during the medical imaging examination, transmit a patient account link using the contact data.

In some embodiments, transmitting the patient account link may involve operating the processor to transmit a patient account completion link that is usable to enable completing the creation of the patient account on the medical imaging system.

In some embodiments, transmitting the patient account link may involve operating the processor to transmit a patient account access link that enables the patient to access the set of medical imaging data acquired during the medical imaging examination.

In some embodiments, the method may involve operating the processor to: determine whether the patient account is associated with the logged-in medical professional account on the medical imaging system; and display a new professional association prompt to initiate an account link between the patient account and the medical professional account when the patient account is not associated with the logged-in medical professional account on the medical imaging system.

In some embodiments, the new patient account prompt may include a new patient account interface having a patient identifier field for receiving the patient identifier.

In some embodiments, the method may involve operating the processor to obtain the set of medical imaging data via a medical imaging application being operated under the logged-in medical professional account.

In some embodiments, the medical imaging application may include an application for obtaining ultrasound imaging data.

In another broad aspect of the present disclosure, there is provided a system for initiating creation of a patient account on a medical imaging system during a medical imaging examination. The system includes a storage component and a processor. The storage component is operable to store patient account data associated with each user account of one or more user accounts on the medical imaging system. The processor is operable to: acquire a set of medical imaging data during the medical imaging examination, the set of medical imaging data being acquired in association with a logged-in medical professional account on the medical imaging system; display a new patient account prompt to initiate creation of the patient account; receive a patient identifier to initiate the creation of the patient account; and use the patient identifier to initiate the creation of the patient account, the patient account to be used for accessing at least a portion of the set of medical imaging data acquired during the medical imaging examination.

In some embodiments, the processor may be operable to display the new patient account prompt while the medical professional account remains logged-in on the medical imaging system.

In some embodiments, the processor may be operable to: initiate the creation of the patient account as a subsidiary account of the medical professional account, the subsidiary account being assigned a lower access level to medical data accessible via the medical imaging system than an access level assigned to the medical professional account.

In some embodiments, after completion of the medical imaging examination, the processor may be operable to: use the patient identifier to request a patient access approval prior to granting access to the set of medical imaging data acquired during the medical imaging examination.

In some embodiments, the patient identifier may include a contact data and the processor may be operable to, after the initiation of the creation of the patient account during the medical imaging examination, transmit a patient account link using the contact data.

In some embodiments, the processor may be operable to transmit a patient account completion link that is usable to enable completing the creation of the patient account on the medical imaging system.

In some embodiments, the processor may be operable to transmit a patient account access link that enables the patient to access the set of medical imaging data acquired during the medical imaging examination.

In some embodiments, the processor may be operable to: determine whether the patient account is associated with the logged-in medical professional account on the medical imaging system; and display a new professional association prompt to initiate an account link between the patient account and the medical professional account when the patient account is not associated with the logged-in medical professional account on the medical imaging system.

In some embodiments, the new patient account prompt may include a new patient account interface having a patient identifier field for receiving the patient identifier.

In some embodiments, the processor may be operable to: obtain the set of medical imaging data via a medical imaging application being operated under the logged-in medical professional account.

In some embodiments, the medical imaging application may include an application for obtaining ultrasound imaging data.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a block diagram of an example system for initiating creation of a patient account during a medical imaging examination, in accordance with at least one embodiment of the present invention. The medical imaging system 100 may include a medical imaging device 102, computing devices 110 and 140, and a server 130. Each of the components of the medical imaging system 100 may be connected by a computer network 120 (e.g., the Internet) to facilitate electronic communication. Each of the components of the medical imaging system 100 may be distributed over a wide geographic area.

The medical imaging device 102 may be configured to generate medical imaging data, such as medical images or data related to medical images (e.g., metadata). The medical imaging device 102 may be operated by a medical professional during a medical imaging examination to generate medical imaging data associated with a patient. The medical imaging device 102 may be an x-ray imager, ultrasound imager, ultrasound scanner or probe, magnetic resonance imaging (MRI) imager, for example. In some embodiments, the medical imaging device 102 may be communicatively coupled to the computing device 110. For example, the medical imaging device 102 may transmit medical imaging data to the computing device 110 for display thereon. In various embodiments, the connection between medical imaging device 102 and computing device 110 may be wired or wireless (e.g., in the example where the medical imaging device 102 is an ultrasound scanner, the connection to the computing device 110 may be wired or wireless). The computing device 110 may then transmit the medical imaging data to the server 130 for storage. In other embodiments, the medical imaging device 102 may directly transmit the medical imaging data to the server 130 for storage.

The medical imaging device 102 may include various components (not shown) for storing software or firmware instructions, configuration settings (e.g., sequence tables in an example where the medical imaging device 102 is an ultrasound scanner), and/or medical imaging data. The medical imaging device 102 may also include one or more processors (not shown) for executing the instructions for performing acts of the methods discussed herein. The medical imaging device 102 may also include various components (not shown) for facilitating electronic communication with other devices, such as the computing device 110. The medical imaging device 102 may communicate with other devices directly, or through the computer network 120.

In some embodiments, the medical imaging device 102 may be an ultrasound scanner. The ultrasound scanner may be configured to transmit ultrasound energy to a target object, receive ultrasound energy reflected from the target object, and generate ultrasound image data based on the reflected ultrasound energy. The ultrasound scanner may include a transducer which converts electric current into ultrasound energy and vice versa. The transducer may transmit ultrasound energy to the target object which echoes off the tissue. The echoes may be detected by a sensor in transducer and relayed through suitable electronics. In some embodiments, the ultrasound scanner may be provided as a handheld ultrasound probe that transmits the ultrasound image data to the computing device 110 for display thereon.

The computing devices 110 and 140 may be a multi-use electronic display device such as a smartphone, tablet computer, laptop computer, desktop computer, or other suitable display device. In various embodiments, the computing devices 110 and 140 may be provided with an input component capable of receiving user input and an output component, such as a display screen, capable of displaying various data. For example, the input component of computing devices 110 and 140 may include a touch interface layered on top of the display screen of the output component. Computing devices 110 and 140 may also include memory, Random Access Memory (RAM), Read Only Memory (ROM), and persistent storage device, which may all be connected to a bus to allow for communication therebetween and with one or more processors. Any number of these memory elements may store software and/or firmware that may be accessed and executed by the one or more processors to perform the methods and/or provide the user interfaces described herein as being performed by or provided on the computing devices 110 and 140. The computing devices 110 and 140 may also include various components for facilitating electronic communication with other devices, such as the medical imaging device 102 or the server 130. The computing devices 110 and 140 may be the same or different type of computing device.

In the illustrated embodiment, the computing device 110 may be operated by a medical professional to control the operation of the medical imaging device 102. For example, certain input received at the computing device 110 may be relayed to medical imaging device 102 to control the operation of the medical imaging device 102. The computing device 110 may also display medical imaging data acquired by medical imaging device 102 or the computing device 110 to the medical professional. For example, the computing device 110 may retrieve medical imaging data from the medical imaging device 102 and/or the server 130. The computing device 110 may also transmit medical image data retrieved from the medical imaging device 102 or acquired by the computing device 110 itself to the server 130 for storage.

In various embodiments, the computing device 110 may execute an application that is configured to communicate with the medical imaging device 102 and/or the server 130. In FIG. 1, this is shown as imaging application or "Imaging App" 112. For example, in embodiments where computing device 110 provides a native software distribution platform (e.g., such as the Apple™ App Store™ for iOS™ devices or the Google™ Play Store™ for Android™ devices), the imaging app 112 may be downloaded therefrom. The imaging app 112 may be configured to perform various acts of the methods described herein as being performed by the computing device 110.

In the illustrated embodiment, the computing device 140 may be operated by a patient to view medical imaging data acquired by the medical imaging device 102 and/or the computing device 110. For example, the computing device 140 may retrieve medical imaging data from the server 130.

In various embodiments, the computing device 140 may also execute an application that is configured to communicate with the server 130. In FIG. 1, this is shown as viewing application or "Viewing App" 142. For example, in embodiments where computing device 140 provides a native software distribution platform (e.g., such as the Apple™ App Store™ for iOS™ devices or the Google™ Play Store™ for Android™ devices), the viewing app 142 may be downloaded therefrom. The viewing app 142 may be configured to perform various acts of the methods described herein as being performed by the computing device 140. In some embodiments, the viewing app 142 and the imaging app 112 may be the same application.

The server 130 may be configured to provide an account service 132 to perform various acts of the methods discussed herein as being performed by the server 130. The server 130 may be accessible at a first network location (e.g., at a Uniform Resource Locator (URL) or at a given Internet Protocol (IP) address). In various embodiments, the account service 132 may be provided in the form of software instructions configured to execute on server 130. For example, the software instructions may provide an Application Programming Interface (API) that the computing devices 110 and 140 are configured to access. The server 130 may include various components, such as a processor and memory, for storing and executing the software instructions. Although illustrated as a single server in FIG. 1, the term "server" herein may encompass one or more servers such as may be provided by a suitable hosted storage and/or cloud computing service. In some embodiments, the server 130 may be provided by two or more servers distributed over a wide geographic area.

The server 130 may be configured to store various data using one or more data storages. The data may be stored in the form of a relational database, object-oriented database, or any other suitable type of database. The data storage(s) may be local to the server 130 or geographically remote to the server 130 and connected via a network. In various embodiments the data stored by the server 130 may be encrypted, hashed, or otherwise secured. In various embodiments, the various data stored in the databases of server 130 may be stored using the database schema shown in FIG. 19.

In the illustrated embodiment, the server 130 may store medical imaging data 138 acquired by the medical imaging device 102 or the computing device 110. For example, the medical imaging data 138 may include images captured by the medical imaging device 102 or data related to the images (e.g., metadata). The server 130 may provide access to the stored medical imaging data 138 to computing device 110 and/or computing device 140. However, the server 130 may restrict access to certain medical imaging data 138 to the computing devices 110 and/or 140.

In various embodiments, the server 130 may be configured to provide and manage a number of user accounts. Each user account may be associated with a respective patient or medical professional, and may be referred to herein as a patient account or medical professional account respectively. The server 130 may define a particular degree of access to the medical imaging data 138 for each patient account and medical professional account. For example, a particular patient account may only be authorized to access medical image data associated with a particular patient. Similarly, a particular medical professional account may only be authorized to access medical image data associated with specific patients under the care of a particular medical professional, and/or medical image data associated with a particular medical institution. In some embodiments, a medical professional may use a medical professional account to assign or adjust the access level of a patient account to the medical image data 138. For example, the medical professional may select a subset of images, metadata (e.g., annotations and/or measurements) that a particular patient account or group of patient accounts is permitted to access. It should be appreciated that the medical professional may assign or adjust the level of patient account access at any time. For example, the medical professional may assign or adjust the level of patient account access during the medical imaging examination, when the creation of the patient account is initiated, and/or after the patient account is created.

In various embodiments, one or more patient accounts may be associated with one or more medical professional accounts. The level of access of a particular patient account may be defined based on an associated medical professional account. For example, a medical professional account may designate a particular level of access for each of the patient accounts associated with that medical professional account. In various embodiments, one or more of the patient accounts may be a subsidiary account to one or more medical professional accounts. The subsidiary account may be assigned a lower (e.g., more restricted) access level to the medical imaging data 138 than that assigned to a medical professional account.

In various embodiments, the server 130 may also be configured to provide one or more administrator accounts. Each administrator account may have unrestricted access to the medical imaging system 100 for performing administration, management, or maintenance on the system. It should be appreciated that the medical professional and patient accounts are distinct from an administrator account.

In the illustrated embodiment, a medical professional account may be required to operate the computing device 110 to use the imaging app 112. Similarly, a patient account may be required to operate the computing device 140 to use the viewing app 142. The server 130 may restrict the access of the computing devices 110 and 140 to specific medical imaging data 138, based on the account used by the patient or medical professional.

The server 130 may store various data 134 and 136 associated with the patient accounts and medical professional accounts. In various embodiments, the server 130 may use the account data 134 and 136 to identify and authenticate patient accounts and medical professional accounts. For example, in order to use a patient account, the computing device 140 may submit one or more credentials to the server 130. In some embodiments, the credentials may include a username and password. Additionally or alternatively, the credentials may be a token, as will be described in further detail herein. Based on the submitted credential(s) and the stored patient account data 136, the server 130 may identify a patient account and determine whether to permit the computing device 140 to use the identified patient account. The server 130 may identify and authenticate medical professional accounts in a similar manner for the computing device 110.

In the illustrated embodiment, the medical imaging system 100 may initiate the creation of a patient account during a medical imaging examination. For example, a medical professional may operate the computing device 110 or the medical imaging device 102 using a medical professional account to acquire medical imaging data associated with a patient. The patient may wish to receive some of the medical imaging data, but may not have a patient account to access the medical imaging data stored on the system 100. During the medical imaging examination, the computing device 110 may direct the medical professional to initiate the creation of a patient account. This may allow the patient to avoid at least a portion of a typical patient account creation process during the medical imaging examination. For example, the medical professional may initiate the creation of the patient account while simultaneously logged-in to the medical professional account. This may eliminate the need for the patient to provide information regarding the medical professional and/or medical imaging data that is typically required to associate the patient account with the medical professional and/or medical imaging data. Subsequent to the medical imaging examination, the patient may operate the computing device 140 using the patient account to access the medical imaging data.

In various embodiments, the server 130 may store various other data in addition to or alternate to the medical imaging data 138. It should be appreciated that the server 130 may also control access to this data based on a patient or medical professional account, in a similar manner. Although the medical imaging system 100 has been described herein with reference to medical imaging data 138 for ease of explanation, it should be appreciated that the medical imaging system 100 may provide controlled access to various other types of data.

As will be understood by persons skilled in the art, the architecture in FIG. 1 is provided for illustration only. Other configurations may be possible in other embodiments. For example, although only one medical imaging device 102, computer network 120, and server 130, and two computing devices 110 and 140 are shown in FIG. 1 for ease of illustration, it should be appreciated that the medical imaging system 100 may include any number of these components.

Figure 2:
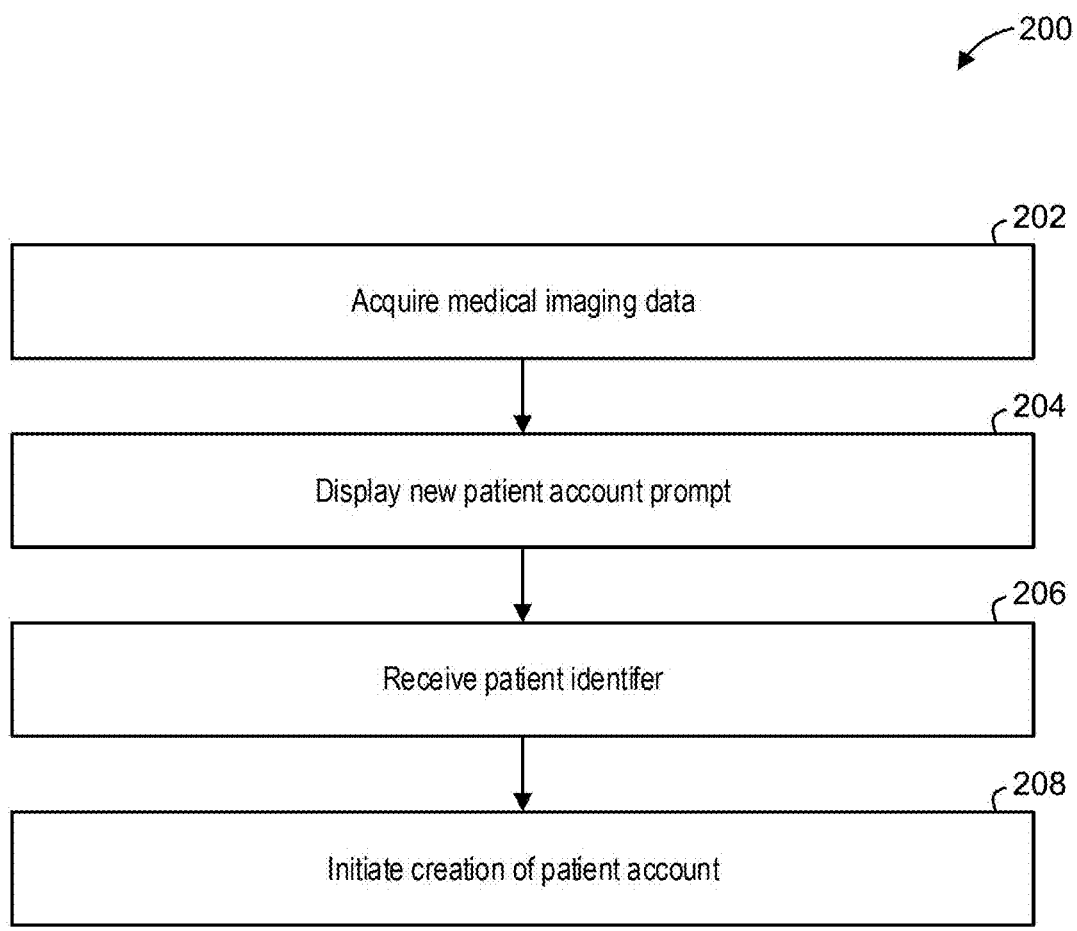
FIG. 2 is a flowchart diagram of an example method of operating the medical imaging system shown in FIG. 1, in accordance with at least one embodiment of the present invention.

Referring to FIG. 2, shown there generally as 200 is a flowchart diagram illustrating an example method of operating the medical imaging system 100, in accordance with at least one embodiment of the present invention. The method 200 may be used to initiate creation of a patient account on the medical imaging system 100 during a medical imaging examination. For ease of illustration, FIG. 2 will be described with reference to the elements of the system o FIG. 1, as well as FIGS. 3-10 which show example user interfaces that may be displayed by the computing devices 110 and/or 140, in accordance with at least one embodiment of the present invention.

At 202, the medical imaging system 100 may acquire a set of medical imaging data 138 during a medical imaging examination. For example, a medical professional may operate the computing device 110 and/or the medical imaging device 102 to capture images of a patient during the medical imaging examination. The medical professional may also operate the computing device 110 or the medical imaging device 102 to collect other information associated with the patient or the images. The set of medical imaging data 138 may be subsequently stored at the server 130.

The set of medical imaging data 138 may be acquired in association with a logged-in medical professional account on the medical imaging system 100. For example, a medical professional may use a medical professional account to operate the computing device 110 or the medical imaging device 102. The medical imaging data acquired by the computing device 110 and/or the medical imaging device 102 using a particular medical professional account.

In various embodiments, the medical imaging data 138 may be acquired via a medical imaging application operated under the logged-in medical professional account. In some embodiments, the medical imaging application may be an application for obtaining ultrasound imaging data. For example, the medical imaging data 138 may be acquired using the imaging app 112 operated under a logged-in medical professional account.

Figure 3:
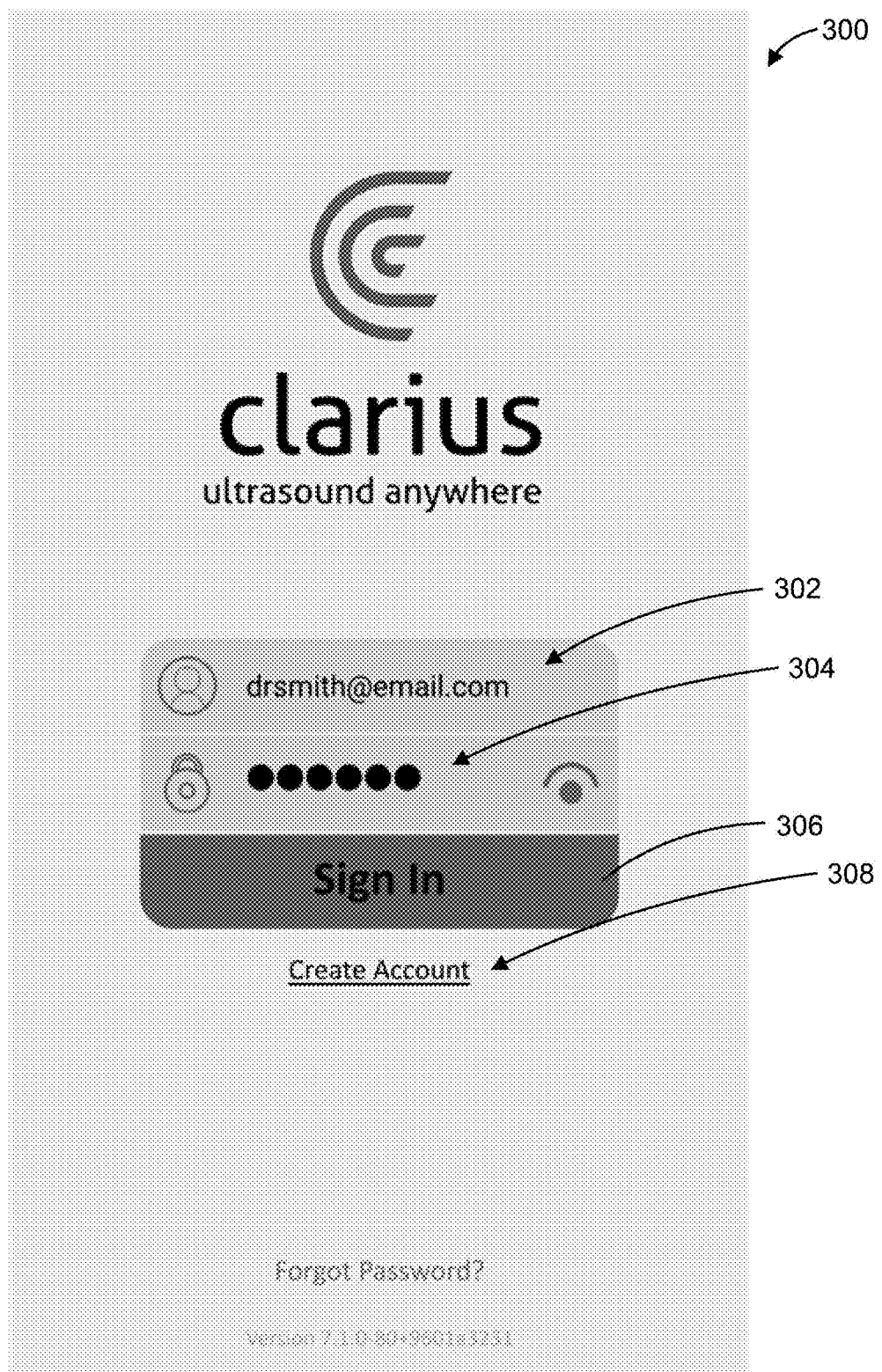
FIG. 3 is an example screenshot of a user interface for logging in to a medical professional account that may be displayed by one or more components of the medical imaging system shown in FIG. 1, in accordance with at least one embodiment of the present invention.

Referring now to FIG. 3, there is shown an example user interface 300 that may be used by a medical professional to login to a medical professional account. The user interface 300 may allow a medical professional to input a username 302 and a password 304. The username 302 and password 304 may be submitted to the server 130 to authenticate the medical professional account by selecting the "Sign In" button 306. The medical professional may be required to login to the medical professional account prior to acquiring medical imaging data. If the medical professional does not have a medical professional account, the medical professional may select the "Create Account" button 308 to create a medical professional account.

Figure 4:
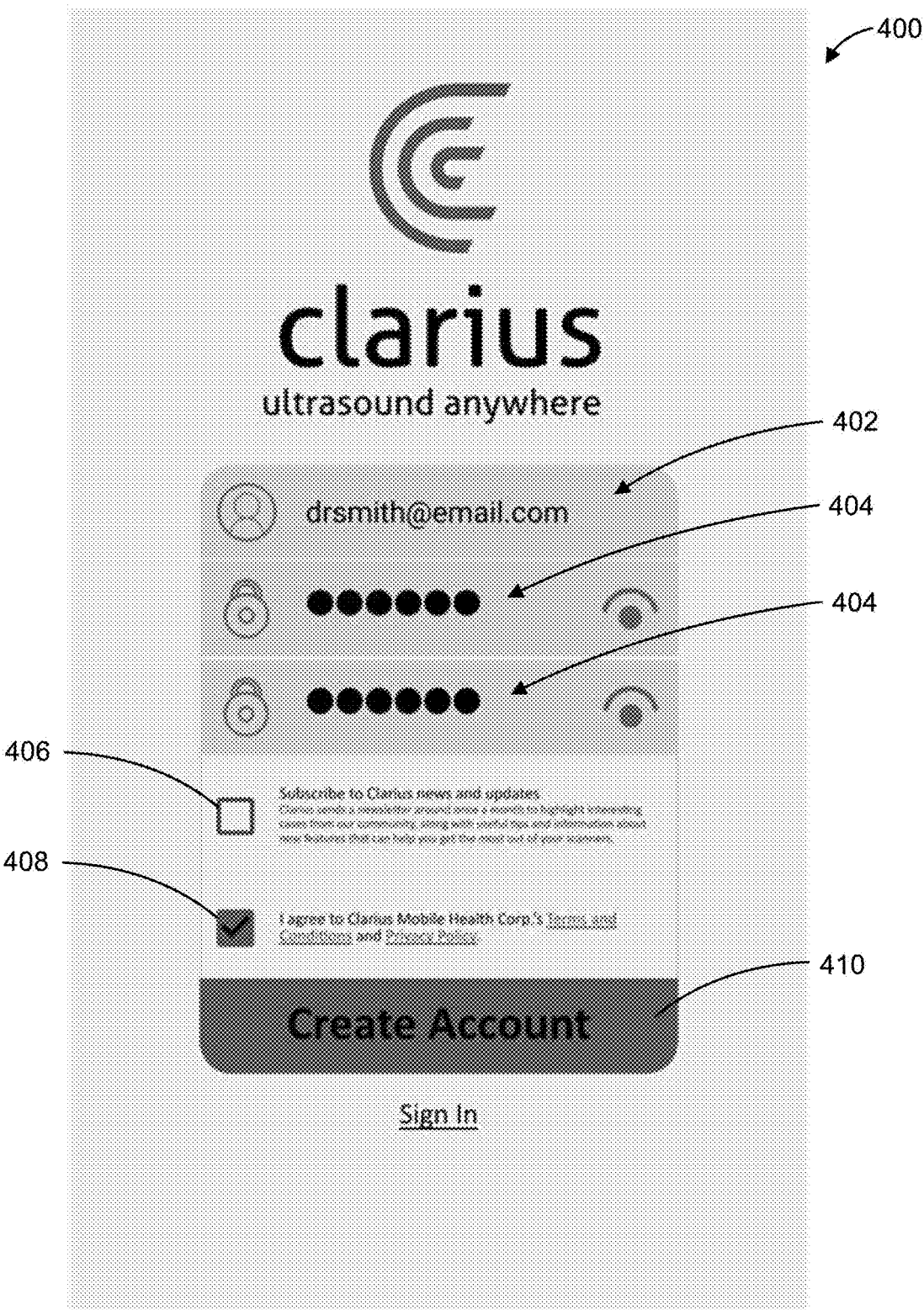
FIG. 4 is an example screenshot of a user interface for creating a medical professional account that may be displayed by one or more components of the medical imaging system shown in FIG. 1, in accordance with at least one embodiment of the present invention.

For example, FIG. 4 shows an example user interface 400 that may be used by a medical professional to create a medical professional account. The medical professional may input a username 402 and password 404. The username and password 404 may be submitted to the server 130 to create the account by selecting the "Create Account" button 410. The medical professional may be prompted by checkboxes 406 and 408 to subscribe to various communications and agree to certain terms and conditions associated with the medical imaging system 100.

In some embodiments, a medical professional may use a token to login to a medical professional account. For example, when a medical professional creates a medical professional account, the medical imaging system 100 may generate a token in association with the medical professional account, and provide the token to the medical professional. The token may be a random sequence of characters (e.g., letters, numbers, symbols, etc.). For example, the medical imaging system 100 may generate the token using a hash function. In some embodiments, this token may be appended to a web link (e.g., a URL) and emailed to the email address of the medical professional.

The token may then be submitted to the server 130 to authenticate the medical professional account. In some embodiments, the token may expire after a predetermined period of time, so that the token does not authenticate the medical professional account after expiry. In some embodiments, receiving an expired token may trigger the medical imaging system 100 to generate and provide (e.g., email) a new, unexpired token to the medical professional. In some embodiments, the medical professional may submit the token by accessing a web address (e.g., a URL) that includes the token. For example, this web address may have been provided to the email address of the medical professional.

Figure 5:
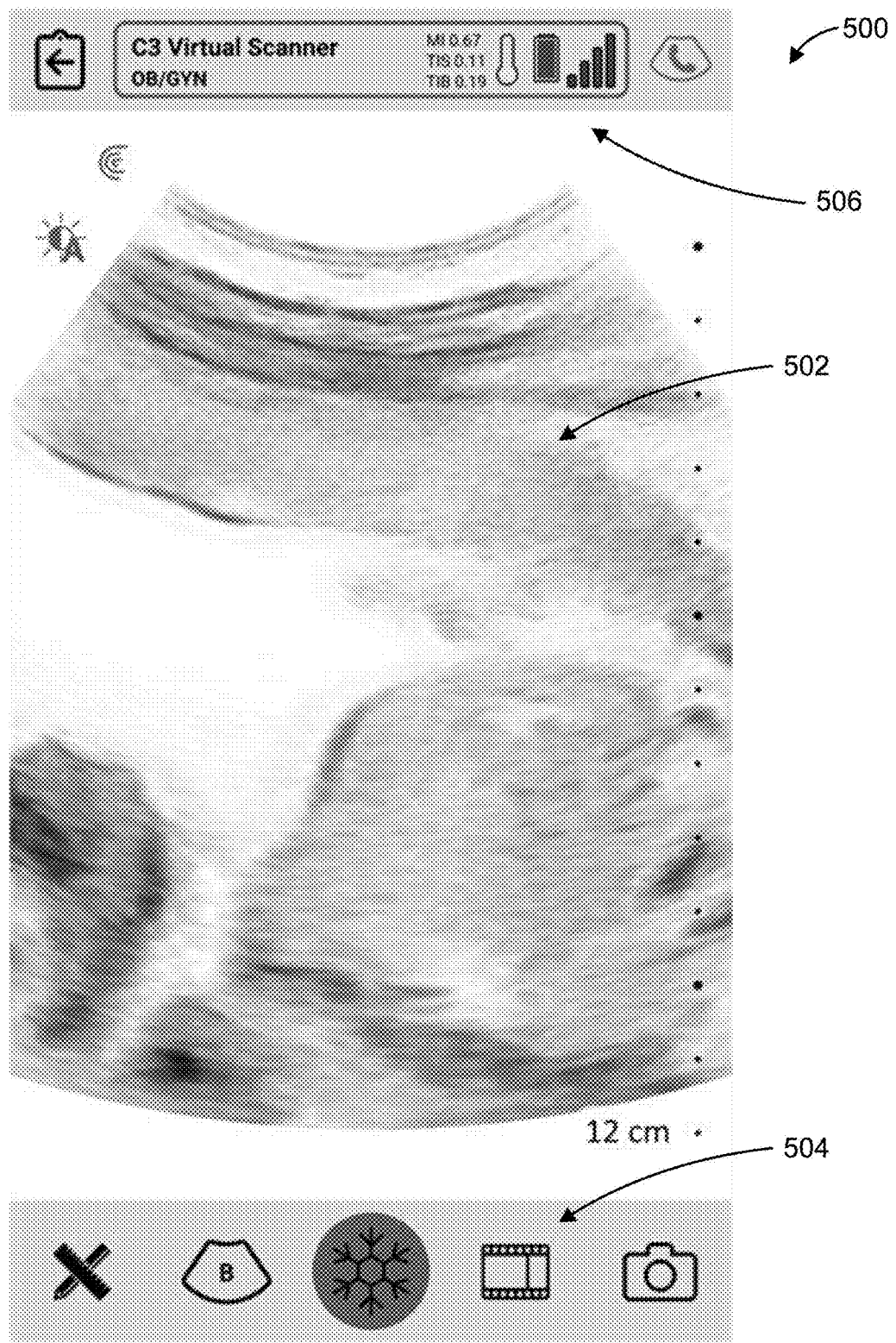
FIG. 5 is an example screenshot of a user interface for acquiring medical imaging data that may be displayed by one or more components of the medical imaging system shown in FIG. 1, in accordance with at least one embodiment of the present invention.

Referring now to FIG. 5, there is shown an example user interface 500 that may be used by a medical professional to acquire medical imaging data 138. In the example of FIG. 5, prenatal ultrasound image data is being acquired, but in various embodiments, other types of medical image data 138 may be possible. The user interface 500 may be unavailable to the medical professional until they are logged-in using a medical professional account. The user interface 500 may include a window 502 showing images being acquired, imaging buttons 504, and status bar 506. The window 502 may display medical imaging data that can be captured at a given time. For example, the window 502 may be used by a medical professional to view and/or alter settings to acquire a better image. The imaging buttons 504 may be selected to trigger the medical imaging device 102 to capture images and/or cineloops, and/or to adjust various settings of the medical imaging device 102. The status bar 506 may display various data associated with the medical imaging device, such as status or setting information.

Figure 6:
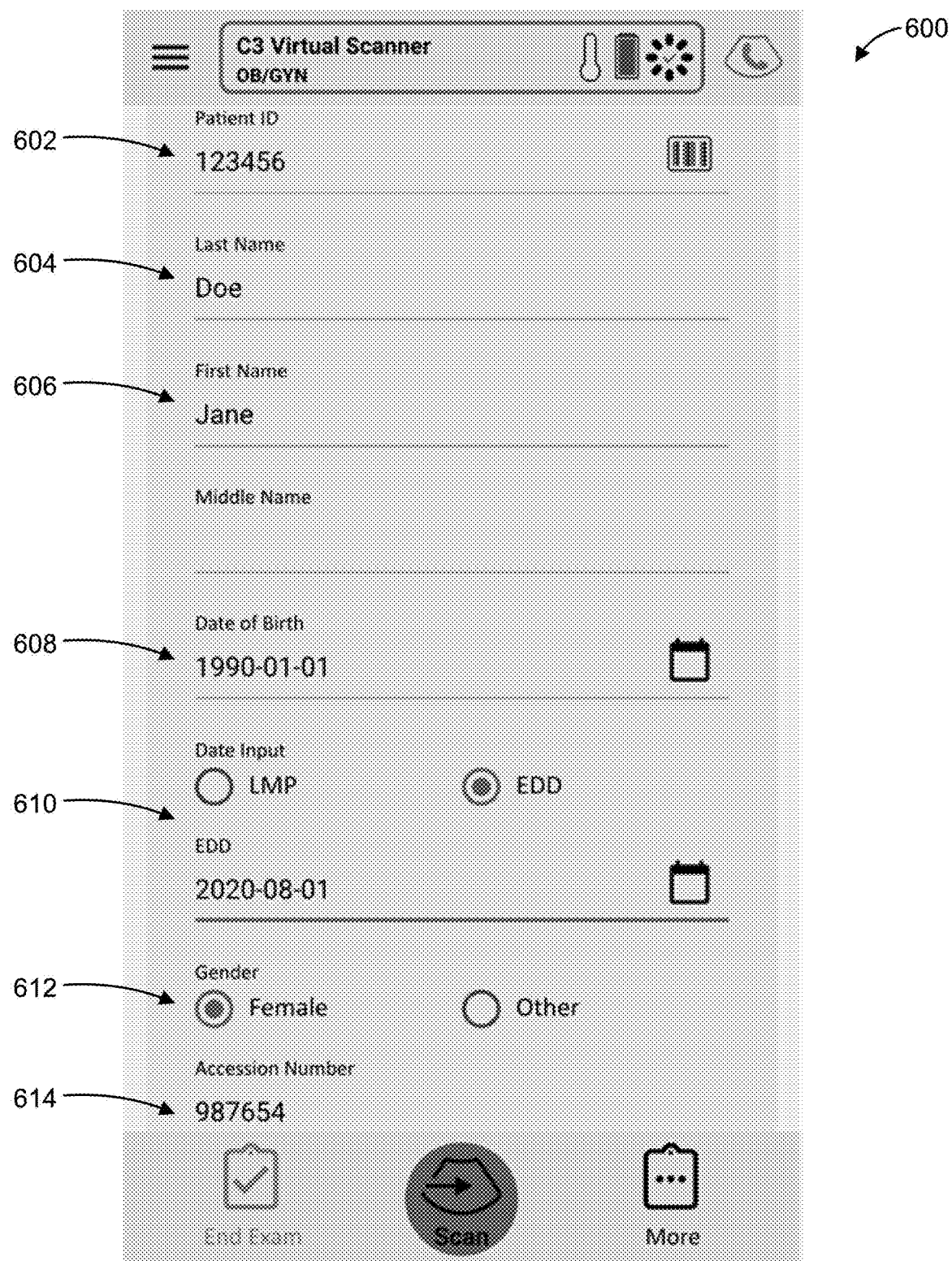
FIG. 6 is an example screenshot of another user interface for acquiring medical imaging data that may be displayed by one or more components of the medical imaging system shown in FIG. 1, in accordance with at least one embodiment of the present invention.

FIG. 6 shows another example user interface 600 that may be used by a medical professional to acquire medical imaging data 138. The user interface 600 may also be unavailable to the medical professional until they are logged-in using a medical professional account. In the illustrated embodiment, the set of medical imaging data 138 may include non-image data, such as metadata. The user interface 600 may include various fields for inputting various data associated with the patient or captured images. For example, the data may include a patient identifier 602, a patient first name 606 and last name 604, a patient date of birth 608, a patient gender 612, an accession number 614, and other data related to the medical imaging acquisition 610.

Referring back to FIG. 2, at 204, the medical imaging system 100 may display a new patient account prompt. The new patient account prompt may allow a medical professional to input various information associated with a patient during the medical imaging examination. For example, the new patient account prompt may request the input of a patient identifier. The patient identifier may be any suitable identifier for identifying the patient. In some embodiments, the patient identifier may include contact data, such as an email, phone number, address, and the like. In other embodiments, the patient identifier may be a code or username associated with the patient.

The new patient account prompt may be displayed while the medical professional account remains logged-in on the medical imaging system 100. For example, the new account prompt may be displayed on the computing device 110 and/or the medical imaging device 102 to a medical professional during the medical examination procedure. As described above, a medical professional may use a medical professional account to operate the computing device 110 and/or the medical imaging device 102 during the medical examination procedure.

Figure 7:
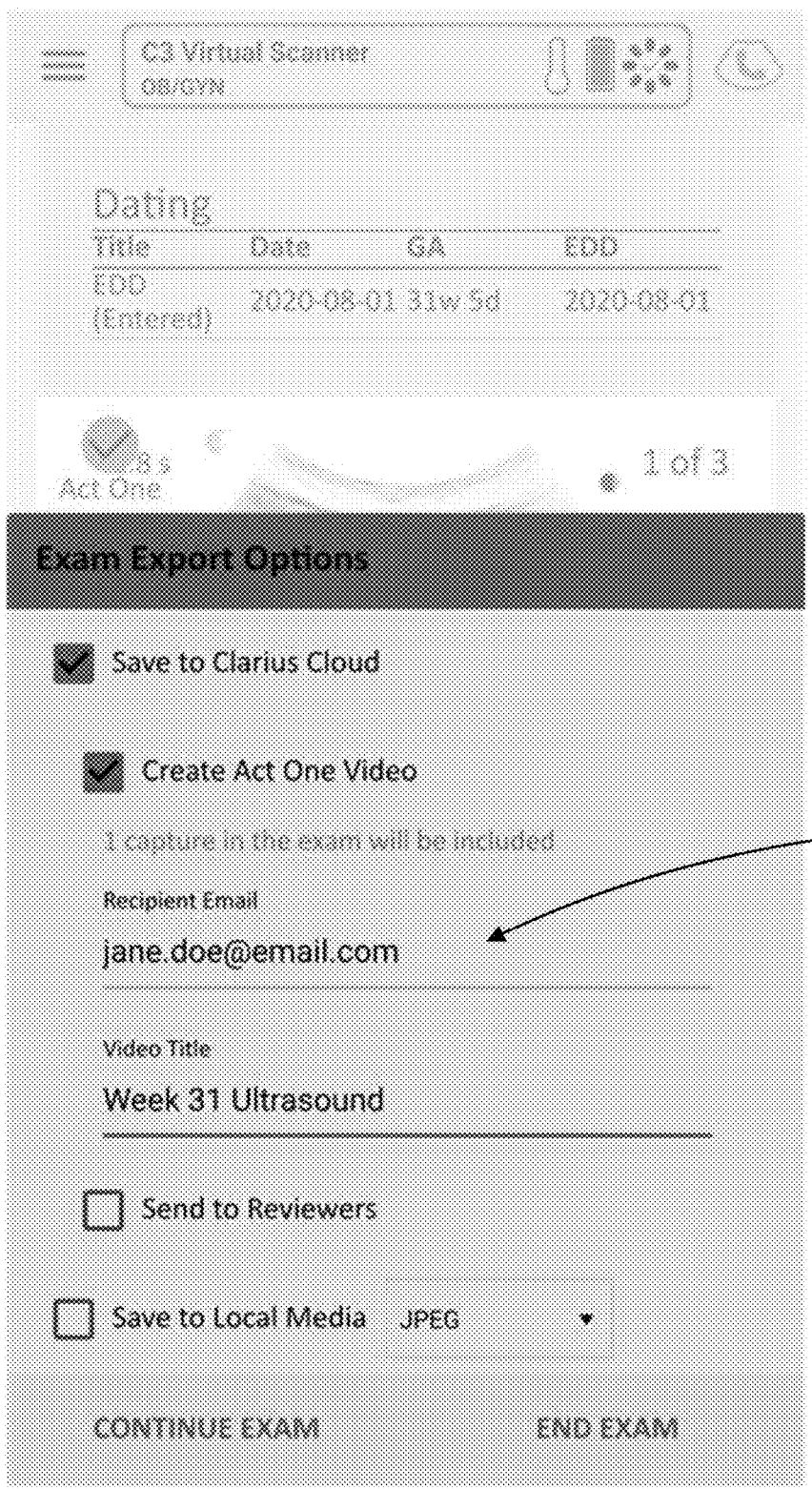
FIG. 7 is an example screenshot of a user interface for initiating creation of a patient account that may be displayed by one or more components of the medical imaging system shown in FIG. 1, in accordance with at least one embodiment of the present invention.

In the example user interfaces discussed herein, the medical imaging data 138 that is being accessed is an obstetrics video of prenatal ultrasound images, and the service for providing this video has the trade name Act One™. In various embodiments, to receive access to the medical imaging data 138, the new patient account prompt may include a new patient account interface having a patient identifier field for receiving the patient identifier. For example, FIG. 7 shows an example user interface 700 that may display the new patient account prompt to a medical professional. In the illustrated embodiment, the user interface 700 may include a field for inputting a patient email address 702 as a patient identifier. The user interface 700 may be displayed on the computing device 110 or the medical imaging device 102 while the computing device 110 or the medical imaging device 102 is logged in to a medical professional account.

In some embodiments, the new patient account prompt can direct the new patient account interface to be displayed to the patient at computing device 140. For example, the new patient account prompt may provide a link (e.g., a URL) for the computing device 140 (e.g., as may be used by a patient) to access a new patient account interface that is being provided by the server 130. In some embodiments, this link may be embedded in the barcode or a Quick Response (QR) code so that the new patient account prompt may display a barcode or QR code on the computing device 110 or the medical imaging device 102. The patient may then operate the computing device 140 (which, in some cases, may be their own mobile computing devices 140) to scan the barcode or QR code to trigger the computing device 140 to access and display the new patient account interface (e.g., in a web browser). The patient may then submit a patient identifier using the new patient account interface displayed on the computing device 140. Barcode or QR code scanning software may be provided on native operating systems of various computing devices 140. For example, such software may be provided in the native camera application on computing devices 140 running the iOS™ operating system.

Configuring the new patient account prompt to provide a link (e.g., display a QR code) for a patient to directly access the new patient account interface on their own computing device 140 may reduce the effort required by the medical professional to receive the patient identifier (e.g., they need only display the barcode or QR code instead of potentially keying in an email address). Such a configuration may also minimize miscommunications between the patient and the medical professional, and/or reduce errors made by the medical professional associated with inputting the patient identifier.

In some embodiments, the medical imaging system 100 may not display a new patient account prompt if a patient is already associated with an existing patient account. For example, the medical imaging system 100 may determine whether the patient is associated with an existing patient account based on the set of medical imaging data 138 acquired at act 202. For instance, the medical imaging system 100 may identify the patient, based on various non-image data (i.e., the patient's name, date of birth, accession number, etc.) inputted during the medical imaging examination, to determine whether the patient is associated with an existing patient account. As a result, the medical imaging system 100 may not initiate the creation of a patient account at 208 when the patient is already associated with a patient account.

Referring back to FIG. 2, at 206, the medical imaging system 100 may receive a patient identifier. The patient identifier may be received in response to the new patient account prompt displayed at 204. For example, the patient identifier may be received from an input received via a new patient account interface displayed at the medical imaging device 102, the computing device 110, and/or the computing device 140. The patient identifier may be used to initiate the creation of the patient account at 208.

At 208, the medical imaging system 100 may initiate creation of a patient account using the patient identifier. The patient account may be used to access at least a portion of the set of medical imaging data 138 acquired during the medical imaging examination. For example, subsequent to the medical imaging procedure, the medical imaging data 138 may be accessed using the viewing app 142 operated under a logged-in patient account.

Figure 8:
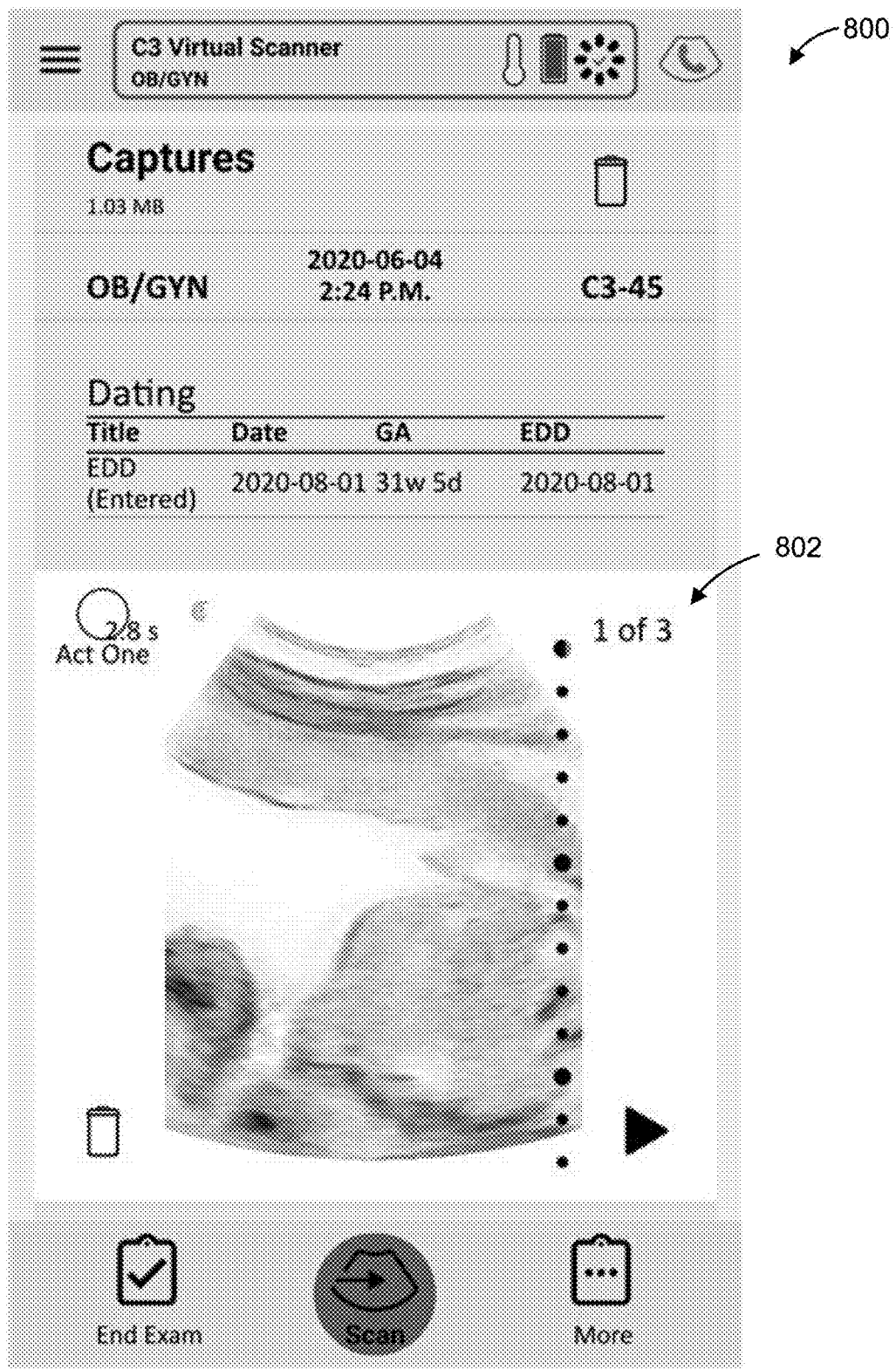
FIG. 8 is an example screenshot of a user interface for approving patient access to medical imaging data that may be displayed by one or more components of the medical imaging system shown in FIG. 1, in accordance with at least one embodiment of the present invention.

In various embodiments, the medical imaging system 100 may allow a medical professional to select which items of the medical imaging data 138 a patient is allowed to access prior to granting access. For example, FIG. 8 shows an example user interface 800 that may be used to grant patient account access to certain medical imaging data 138. In the illustrated embodiment, a medical professional may use the preview window 802 to select one or more images, cineloops, and/or other data captured during the medical examination to be shared with the patient. For example, the medical professional may permit the patient to access the high quality and relevant images, while limiting patient access to low quality, unhelpful, or other images that the medical professional may not wish to share with the patient. For example, in an example embodiment where the medical imaging data 138 are prenatal ultrasound images, the medical professional may only select ultrasound images for patient access where certain anatomy of the fetus is easily discernible by a non-medical layperson (e.g., an image that shows the profile of the fetus). They may decide to not provide access to ultrasound images which are overly technical or contain measurements and/or annotations that are obscure the viewing of the fetus.

In various embodiments, the medical imaging system 100 may display a new medical professional association prompt to initiate an account link between a patient account and a medical professional account. For example, the medical imaging system 100 may determine whether the patient account is associated with the logged-in medical professional account and display the prompt if they are not associated. The medical professional may use the prompt to associate the logged-in medical professional account with the patient account. However, in some embodiments, this prompt may not be displayed at all. For example, the system 100 may assume that all patient accounts created from a new patient account prompt displayed when a medical professional account is logged-in will be linked to the logged-in medical professional account.

Referring back to FIG. 2, in some embodiments, the patient account may be fully created at 208. For example, the patient identifier and/or the acquired set of medical imaging data 138 may include all of the required information to complete the creation of the patient account. In other embodiments, the creation of the patient account may not be fully completed at 208. For example, the patient identifier or the acquired set of medical imaging data 138 may not include all of the required information required to complete the creation of the patient account. Instead, the creation of the patient account may only be initiated (e.g., partially completed) during the medical imaging examination, and the patient account may be completed subsequent to the medical examination procedure. This process may encourage the creation of patient accounts, as the patient is not required to provide large amounts of the information during the medical imaging examination to initiate creation of the patient account, which may otherwise be tedious or time-consuming.

In various embodiments, the medical imaging system 100 may transmit a patient account link upon the patient account creation being initialized. For example, the patient account link may be transmitted to the patient and accessed by the patient using the computing device 140. The patient account link may be transmitted based on the contact data of the patient identifier. For example, where the patient identifier is an email, the patient account link may be emailed to the patient.

Figure 9:
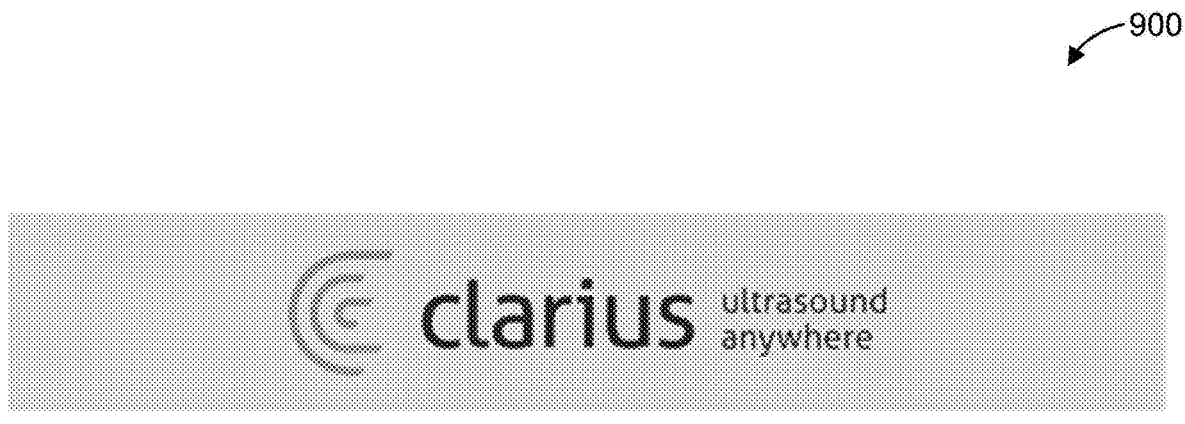
FIG. 9 is an example screenshot of a user interface for completing creation of a patient account that may be displayed by one or more components of the medical imaging system shown in FIG. 1, in accordance with at least one embodiment of the present invention.
Figure 9:

In some embodiments, the patient account link may be a patient account completion link that is usable to enable completing the creation of the patient account. For example, the patient account completion link may request input of additional information for completing the patient account. Referring back to FIG. 4, the patient account link may, for example, request a username 402, a password 404, or other information, in a similar manner as user interface 400. Additionally or alternately, the patient account link may request a simple confirmation. For example, FIG. 9 shows an example user interface 900 for simply confirming the creation of the patient account. In the illustrated embodiment, a patient may select the "Verify Account" button 902 to confirm and complete the creation of the patient account.

In some embodiments, the patient account link may provide one or more credentials that can be used by a patient to login to the patient account. For example, the patient account link may provide the patient with a username and/or password. Additionally or alternatively, the patient account link may provide the user with a token. As discussed above, a token may be a random sequence of characters (e.g., letters, numbers, symbols, etc.). For example, the medical imaging system 100 may use a hash function to generate the token. In some embodiments, the token may expire after a predetermined period of time, so that the token does not authenticate the patient account after the token has expired. In some embodiments, receiving an expired token may trigger the medical imaging system 100 to generate a new, unexpired token, and transmit another patient account link that includes the new token.

Similar to the tokens that may be used to authenticate medical professional accounts, it may be possible to append the token to a web address or URL that forms the link sent to a patient identifier (e.g., a patient email address or phone number). In this manner, the web address may include a token associated with a patient account so that the token is submitted when a patient accesses the web address. Put another way, accessing the URL will implicitly provide the token to the server 130. The server 130 may then perform authentication based on the provided token.

Figure 10:
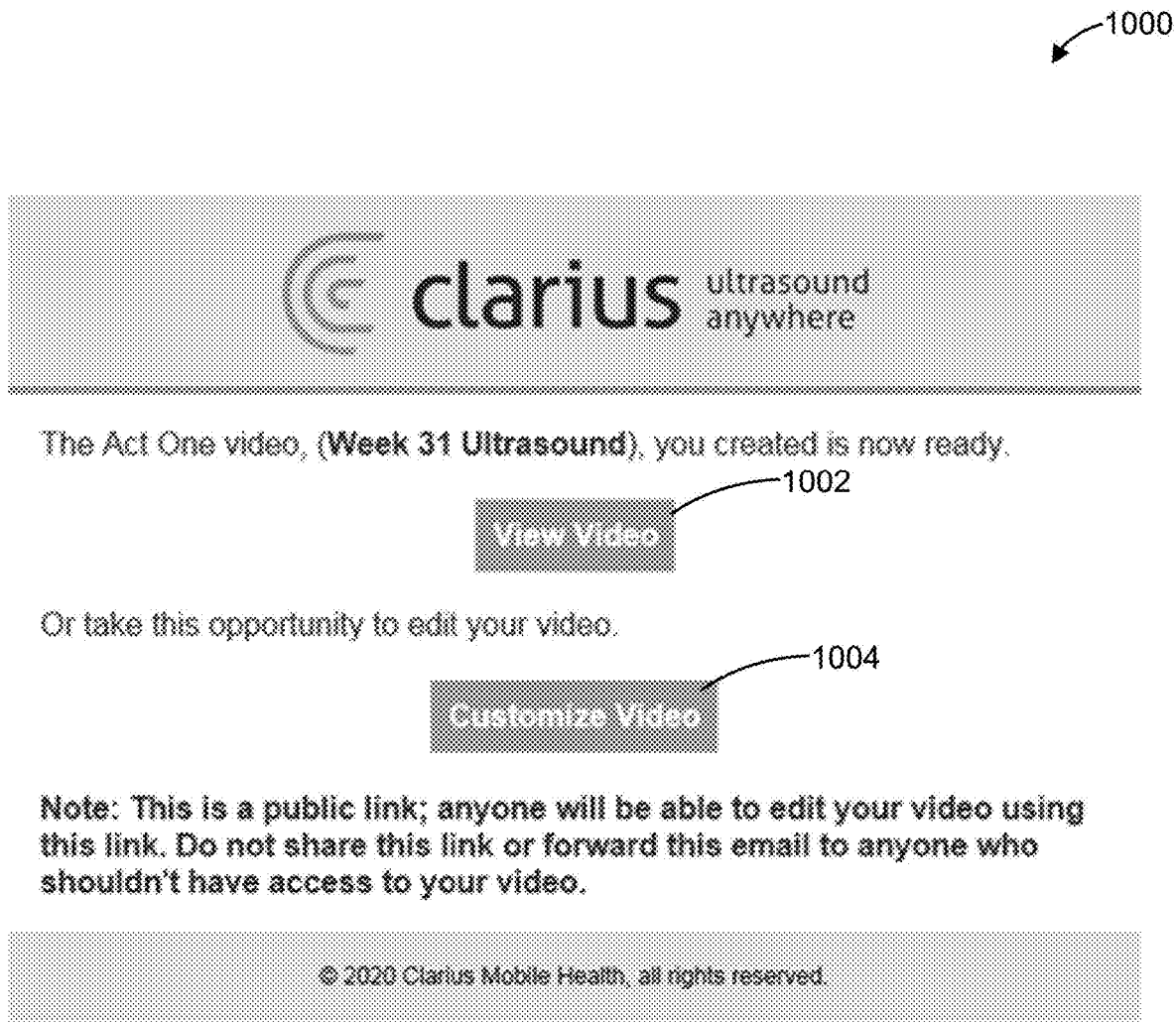
FIG. 10 is an example screenshot of a user interface for viewing medical imaging data that may be displayed by one or more components of the medical imaging system shown in FIG. 1, in accordance with at least one embodiment of the present invention.

In some embodiments, the patient account link may be a patient account access link that enables the patient to access the set of medical imaging data 138 acquired during the medical imaging examination. For example, FIG. 10 shows an example user interface 1000 that may provide patient access to the medical imaging data 138. In the illustrated embodiment, a patient may select the button 1002 to view a video associated with the acquired set of medical imaging data 138 related to fetal ultrasound images. Alternately, the patient may select the button 1004 for editing a video associated with the acquired set of medical imaging data 138.

Referring now to FIGS. 11-18, shown there are example user interfaces that may be displayed by the computing devices 110 and/or 140 (as shown in FIG. 1), in accordance with at least one embodiment of the present invention. In a particular example embodiment, the user interfaces may be displayed on computing device 140 and permit a patient to use a patient account to access the at least some of the medical imaging data 138 from the medical imaging system 100. In the example embodiments of FIGS. 11-18, the medical imaging data 138 to be accessed may be obstetrics images and/or cineloops of a fetus that may be acquired during a pregnancy, and where the medical imaging data 138 can be reformatted in the form of a keepsake video with decorative elements to enhance viewing of the medical imaging data 138. As noted above, the service for providing access to such a video has the trade name Act One™.

Figure 11:
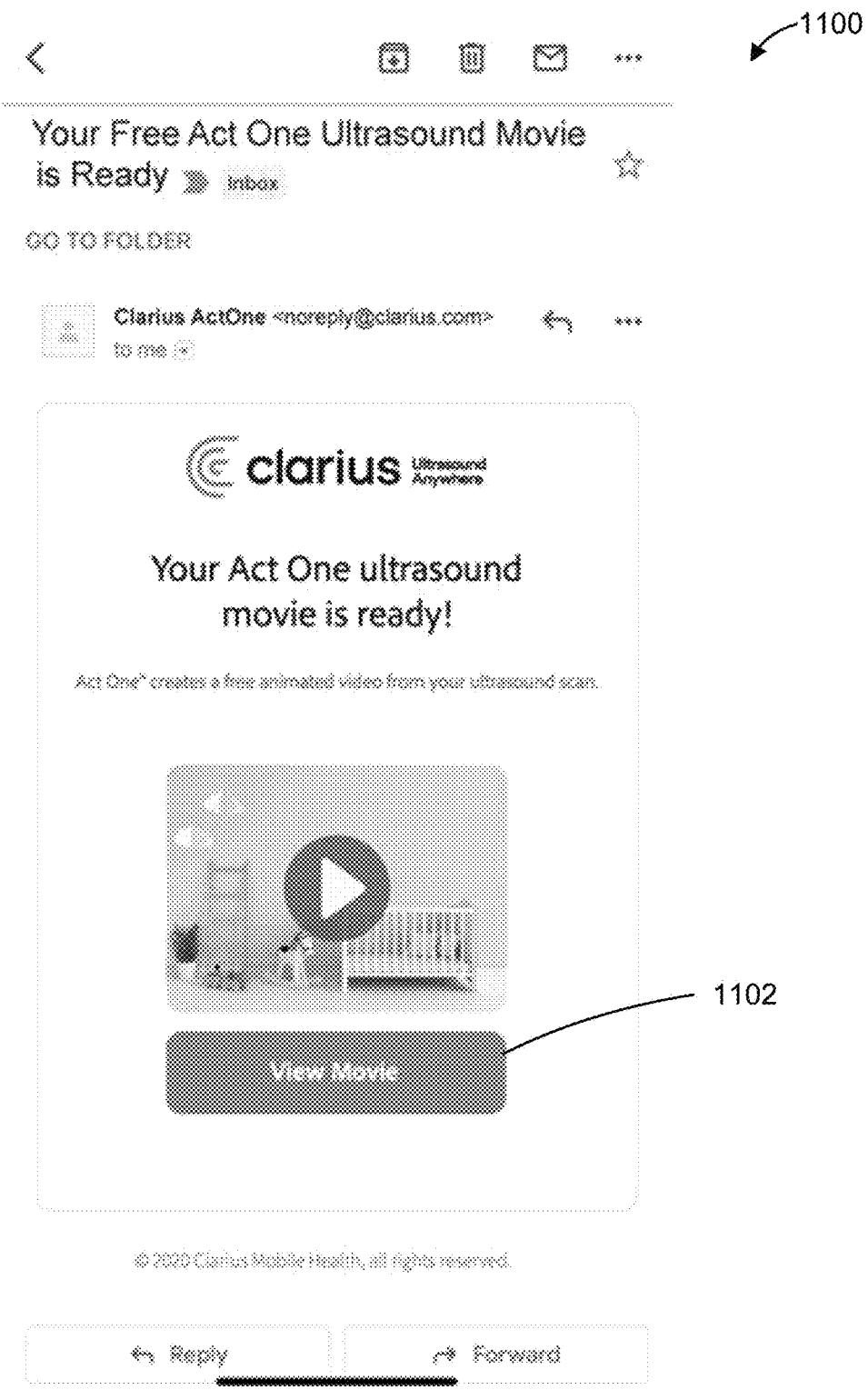
FIGS. 11-18 are example screenshots of a user interface for viewing medical imaging data that may be displayed by one or more components of the medical imaging system shown in FIG. 1, in accordance with at least one embodiment of the present invention.

FIG. 11 shows an example user interface 1100 that can allow a patient to access a patient account. For example, the user interface 1100 may be displayed in an email application at the patient computing device 140 after they have inputted a patient identifier (e.g., an email address) into a new patient account interface. In the illustrated example, a patient can select the "View Movie" button 1102 to login to a patient account. In some embodiments, the button 1102 may direct the patient to a login interface. For example, referring back to FIG. 3, the login interface may request a username 302 and a password 304 associated with a patient account, in a similar manner as user interface 300. Additionally or alternatively, a token associated with a patient account can be submitted to the medical imaging system 100 in response to the patient selecting the button 1102. For example, the button 1102 may direct the patient to a web address that includes the token. The web address may lead to a web service for providing access to the medical imaging data 138. The web service may, for example, be provided by server 130 (as shown in FIG. 1). The medical imaging system 100 can then authenticate the username, password, and/or token to determine whether or not to grant access to the patient account. In various embodiments, the patient may be prevented from accessing the user interfaces shown in FIGS. 11-18 (and therefore the medical imaging data 138), unless the patient account is successfully authenticated. In various embodiments, a successful authentication may result in the server 130 displaying the example user interfaces of FIGS. 12-18.

Figure 12:
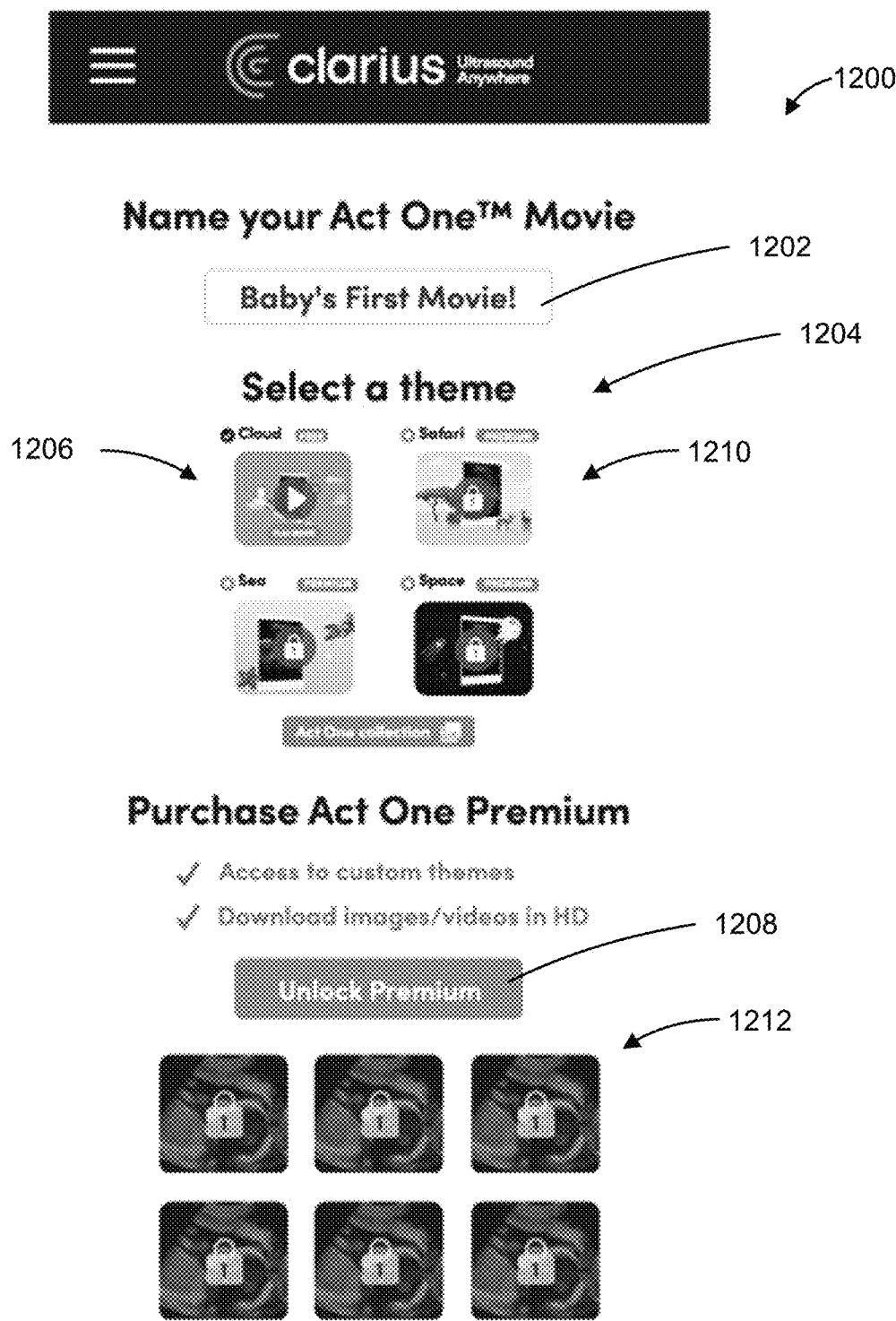

FIG. 12 shows an example user interface 1200 that can allow viewing, editing, and/or downloading one or more videos associated with the medical imaging data 138. In the illustrated example, a patient can edit the name of the name of the video using the text field 1202. Also, the patient may select one or more editing options 1204 to edit the video. In the illustrated example, the editing options 1204 may allow the patient to add a theme to a video by adding one or more graphical elements (e.g., a border) and/or one or more audio elements (e.g., music or other sound effects). For example, the patient may select one of several viewing selections 1206 (e.g., pre-made theme options) for the video. In some embodiments, upon selecting a viewing selection 1206, the patient may be directed to example user interface 1300 shown in FIG. 13.

Figure 13:
Figure 14:
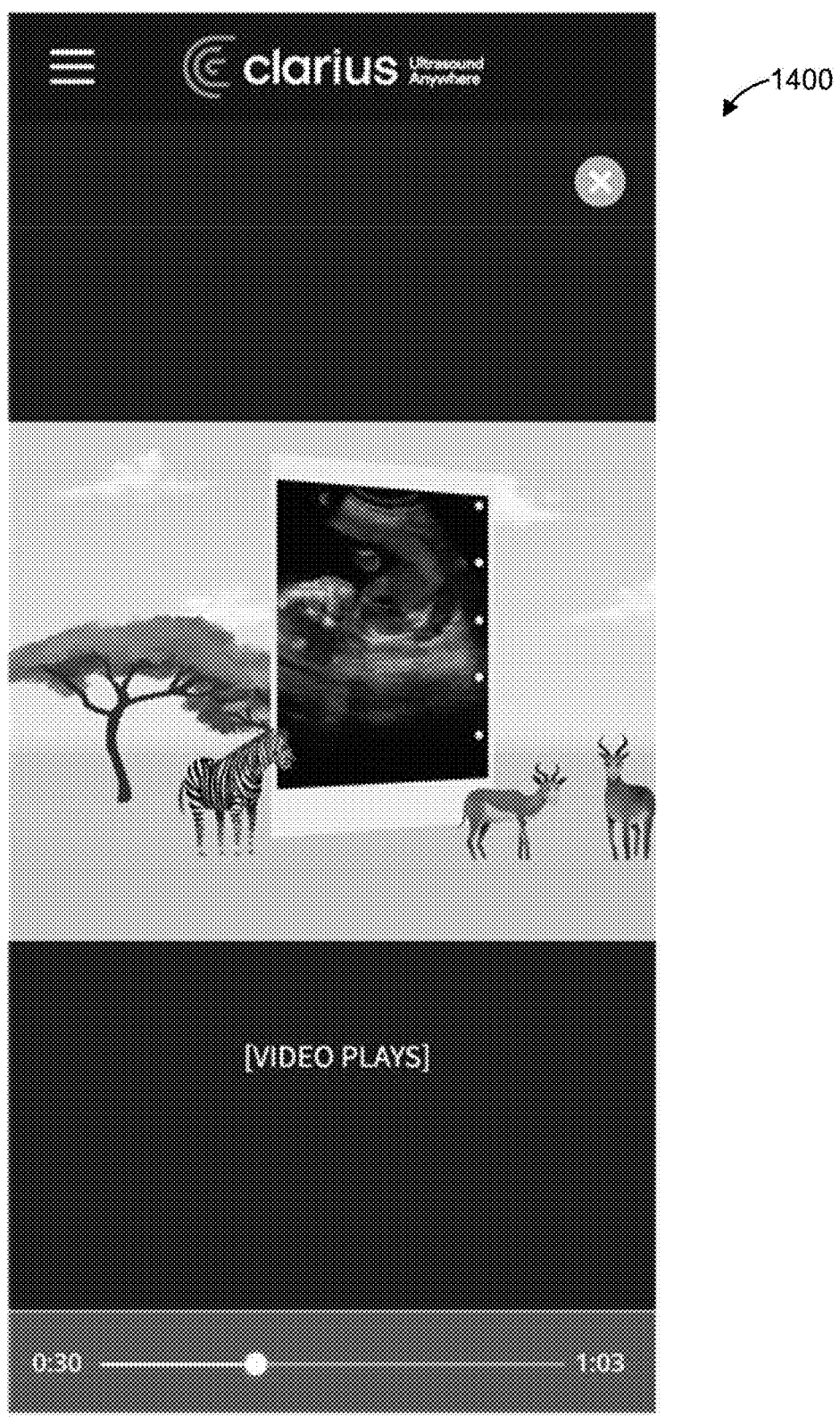

FIG. 13 shows an example user interface 1300 that can allow a patient to view and/or share a video associated with the medical imaging data 138. In the illustrated example, a patient may share a video (e.g., to provide access of the video to another party that is neither the patient nor the medical professional) by selecting one or more of the sharing tools 1304. The patient may also view the video by selecting the play button 1302. For example, FIG. 14 shows an example video playing user interface 1400 for video playback.

Figure 15:
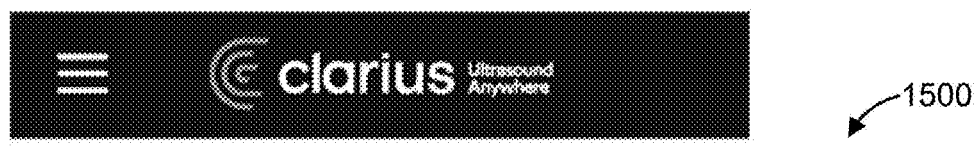
Figure 15:
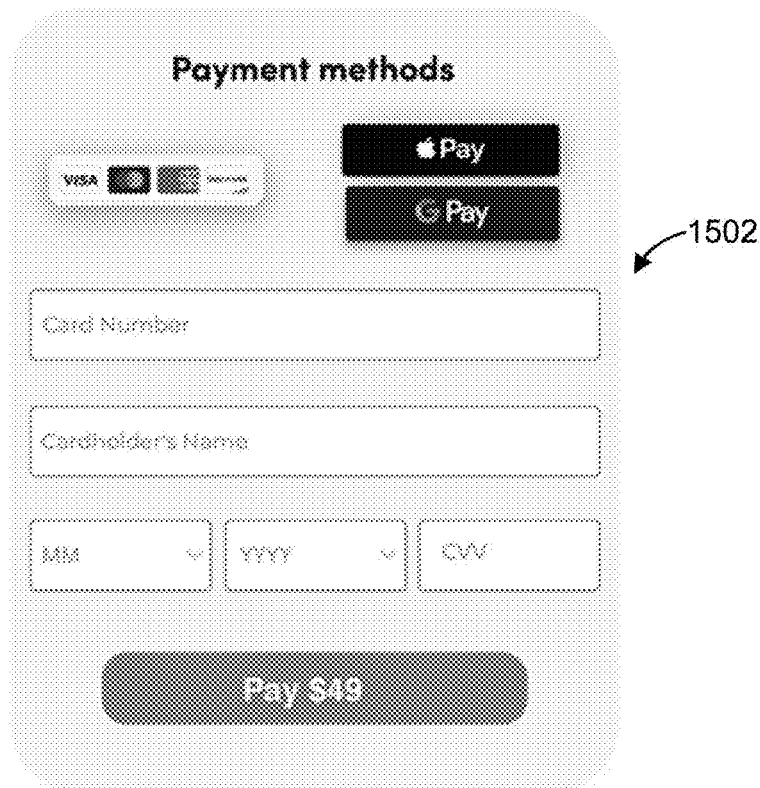
Figure 15:
Figure 16:
Figure 16:
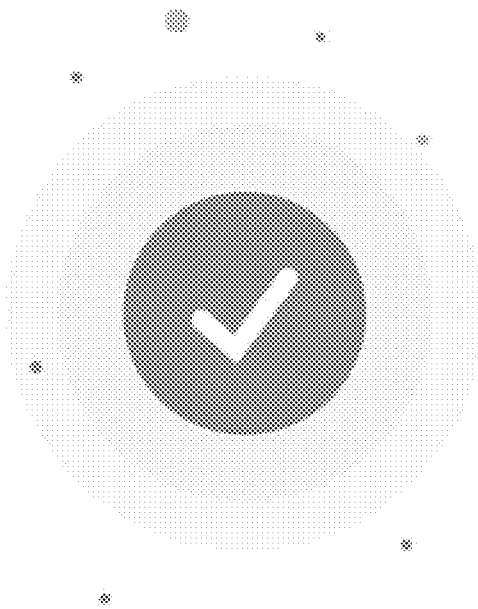
Figure 16:
Figure 17:
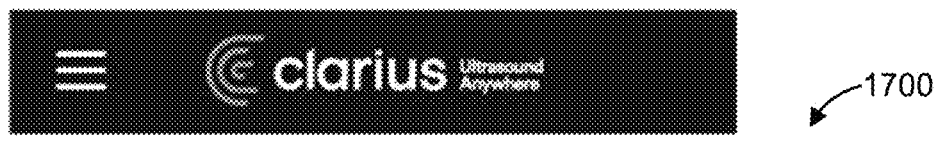
Figure 17:
Figure 17:
Figure 17:
Figure 17:
Figure 17:
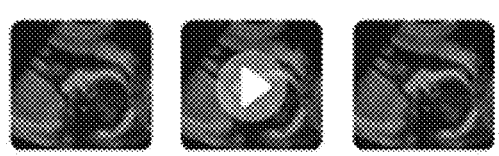
Figure 17:
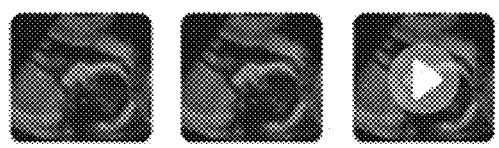
Figure 17:
Figure 18:
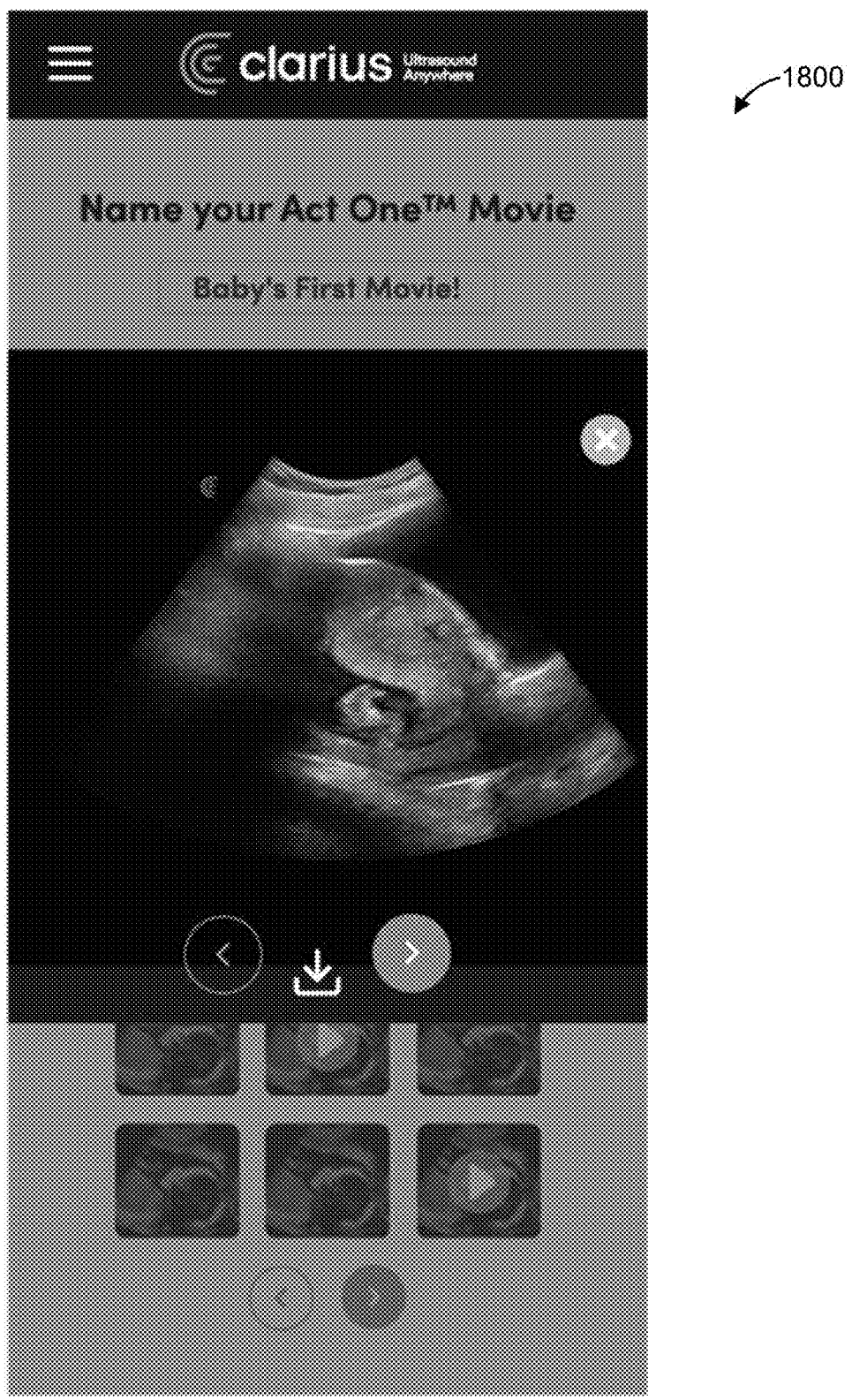

In some embodiments, one or more features for accessing the medical imaging data 138 may be restricted only to patient accounts that have paid for the feature(s). For example, referring back to FIG. 12, access to downloading high resolution videos 1212 and to the viewing of certain editing selections 1210 may be restricted. In order to access the restricted features, a patient can select the "Unlock Premium" button 1208 to pay for the restricted features. For example, FIG. 15 shows an example user interface 1500 that may allow a patient to pay to unlock the restricted features. In the illustrated example, the patient can submit payment information using the payment form 1502. Upon successful payment, the patient can then access the restricted features. For example, FIG. 16 shows an example user interface 1600 for confirming successful payment by the patient. FIG. 17 shows an example user interface 1700 with the restricted features now unlocked (e.g., downloading high resolution videos 1712 and the ability to access/view certain editing selections 1710). FIG. 18 shows an example user interface 1800 for downloading high resolution videos that can be accessed by selecting one of the download selections 1712 in FIG. 17.

Figure 19:
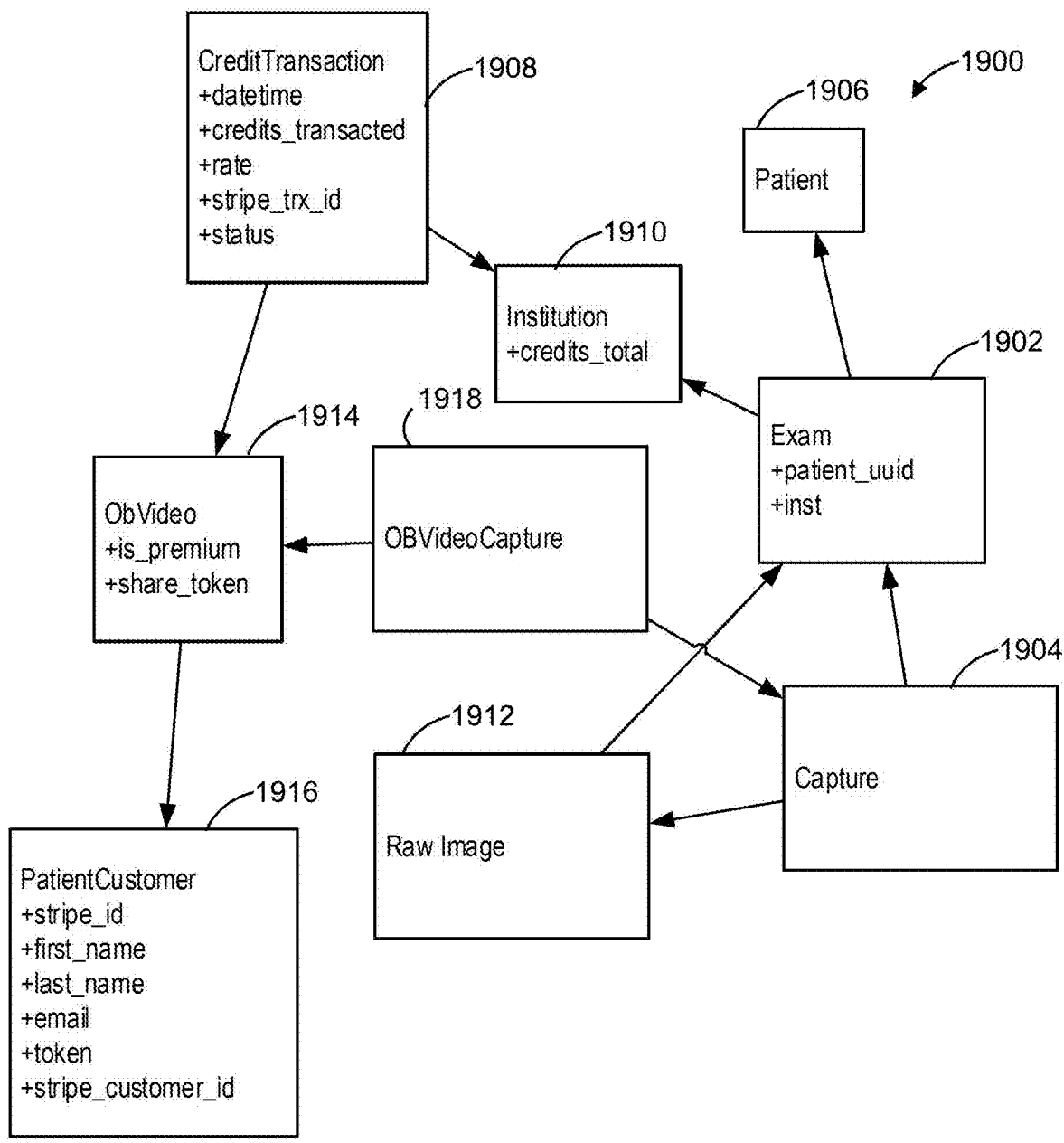
FIG. 19 is a block diagram of an example database schema for storing medical imaging data that may be used by the medical imaging system shown in FIG. 1, in accordance with at least one embodiment of the present invention.

Referring now to FIG. 19, shown there generally as 1900 is a block diagram illustrating an example database schema for storing medical imaging data, in accordance with at least one embodiment of the present invention. For example, the database schema 1900 may be used to store the patient accounts 136 and/or the medical imaging data 138 in the medical imaging system 100 shown in FIG. 1 above.

As shown in FIG. 19, the database 1900 can include a number of related datasets (also referred to as tables). In the illustrated example, the datasets include "Exam" 1902, "Capture" 1904, "Patient" 1906, "Credit Transaction" 1908, "Institution" 1910, "Raw Image" 1912, "ObVideo" 1914, and "PatientCustomer" 1916.

Each dataset can include one or more associated fields or attributes. For example, the "Exam" dataset 1902 may include the fields "patient_uuid" and "inst", which, for a particular medical imaging examination, correspond to a patient identifier and an institution identifier associated with that examination. In various embodiments, these fields may be foreign keys that reference the "Institution" dataset 1910 or the "Patient" dataset 1906 respectively. In the illustrated example, these relationships are shown as logical connection arrows between the datasets.

In the illustrated example, the "Capture" dataset 1904 may correspond to the various medical images and media (e.g., as selected by a medical professional to be associated with a given examination record). Each captured item for the "Capture" dataset 1904 may simply be an image or cineloop, but there may also be underlying raw ultrasound data associated with such image or cineloop (e.g., pre-scan converted ultrasound data in polar coordinates before it has been scan converted to cartesian coordinates). This is reflected in the "Raw Image" dataset 1912, which may itself also be logically linked to an associated record in the "Exam" dataset 1902.

The example database schema of FIG. 19 corresponds to the example screenshots of FIGS. 11-18 above where the medical imaging data 138 to be accessed may be obstetrics images and/or cineloops of a fetus that may be acquired during a pregnancy, and where the medical imaging data 138 can be reformatted to be a keepsake video with decorative elements to enhance viewing of the medical imaging data 138. In this example embodiment, the database schema 1900 may also have an "ObVideo" 1914 table 1914 for the keepsake video, where such records may be associated with elements in a "OBVideoCapture" dataset 1918. For example, the various particular data elements of an "OBVideoCapture" dataset 1918 may be multimedia elements that have decorative elements added to the underlying image or cineloop in the "Capture" 1904 dataset.

The "ObVideo" dataset 1914 may have a field "share token" that stores the token that can be used externally to access a given "ObVideo" entry. For example this token may a string of characters appended to the URL in the user interface element 1304 of FIG. 13. The URL with this token may, for example, be provided by an expecting mother to her friends and family.

In the example of FIG. 19, the "ObVideo" dataset 1914 may also have a field "is_premium" set to true if a given OB video record was generated as part of a premium feature (e.g., as may have been unlocked via user interface element 1208 in FIG. 12). As noted above, premium features may be purchased in some embodiments (e.g., payment may be received by using interface 1500 in FIG. 15). In these transactions, the record in the "ObVideo" dataset may have an associated entry in the "CreditTransaction" table 1908. The "CreditTransaction" table 1908 may store data related to payment information (e.g., containing fields "datetime" for when the transaction occurred, "stripe_trx_id" for a payment processor transaction identifier using a payment platform (e.g., in the example, the payment processor Stripe™ is used), "rate" to reflect the payment rate or price for the feature, and the "status" of the transaction).

In some embodiments, the payment transaction may also be associated with a credit system that allows customers to accumulate credits and/or redeem them for premium features. In the illustrated example, the "CreditTransaction" dataset 1908 may also include a field "credits transacted" to reflect a number of credits earned and/or redeemed by the payment transaction. In some embodiments, the credit balance may be stored at the institution level, so that the "CreditTransaction" dataset 1908 may then also be associated with the "Institution" dataset 1910 which in the illustrated example also contains a "credits_total" field which may get updated based on the "credits_transacted" value of a "CreditTransaction" record.

Referring still to the example database schema of FIG. 19, various data associated with a patient accounts 136 (as shown in FIG. 1) may be represented by a "PatientCustomer" dataset 1916. As shown, the "PatientCustomer" dataset 1916 may store, for each patient account, the patient's name ("first_name" and "last_name"), identifier (e.g., "email"), login credentials (e.g., "token"), and payment information (e.g., "stripe_id" and "stripe_customer_id").

As noted above, the "token" field in the "PatientCustomer" may be used to authenticate a user prior to the user being permitted access to a particular record in the "ObVideo" dataset 1914. This "token" can be set to expire, and if a user is attempting to access medical image data 138 using a token that is already expired, this may prompt an email being sent to the email address indicated in the "email" field with a newly-generated token. In some embodiments, this token alone may be used for authenticating a user when access is attempted. E.g., provided a user attempting to access the medical image data 138 uses the correct token (which generally would only be accessible from the email address account specified in the "email" field), it can be presumed that such user is authorized to access the medical image data. This can be considered a form of email account trust that presumes access to the email address account used to communicate the token (either new or refreshed upon expiry) signifies that the user is legitimately authorized. In these embodiments, user authentication may be simplified as typical account creation steps related to use of a username and creation of a password can be omitted.

Notable in the database schema 1900 of FIG. 19 is that the "PatientCustomer" dataset 1916 is stored separate from the "Patient" dataset 1906, such that the two need not be the same. While the term "Patient" is included in the name of the dataset 1916, in various embodiments, this dataset need not be related to patients at all. For example, this dataset can be used to store information about any external person or entity for which it may be desirable to access the medical image data 138 (a record in the "ObVideo" dataset 1914). For example, in the case where the medical image data 138 corresponds to an obstetrics video, it may be desirable for the father of the unborn baby to access the video, but the father would not be the patient in that scenario.

The data related to the "Patient" dataset 1906 and associated "Exam" 1902 data may thus be considered patient medical records. In situations where the "PatientCustomer" record is in fact the same person as referred to by the "Patient" record, it may be possible to pre-populate certain columns of the "PatientCustomer" (e.g., "first_name" and "last_name") from the patient medical record. However, by distinguishing the "PatientCustomer" data from the patient medical record, it allows for greater flexibility for authorized non-patients to access the medical imaging data (e.g., for the father of an unborn baby to access an obstetrics video, as noted).

In another example, the customer dataset 1916 may not necessarily be a customer at all in that no financial transaction may need to occur. Instead, the dataset 1916 may simply be an account for allowing authorized external access to the medical image data. For example, in the example where obstetrics ultrasound media is obtained during a pregnancy, the exam media may be acquired by a sonographer at a radiology clinic, and it may be desirable to allow a referring family physician or primary care provider access to the ultrasound media. In this scenario, the dataset 1916 may store information (e.g., the email address) about the referring healthcare practitioner, so as to provide them with an account that allows them access to the medical image data of their patient.

Further variations may be possible. For example, it may be possible for a single set of medical image data 138 to be accessible by multiple records in the "PatientCustomer" dataset 1916 or there may be multiple "email" fields in the "PatientCustomer" dataset 1916. This may allow the same set of medical image data 138 to be accessed by multiple parties (e.g. a father of an unborn baby and the primary family doctor of the expecting mother).

In further variant embodiments, a single user represented by a record in the "PatientCustomer" dataset 1916 may be associated with multiple sets of medical image data 138. For example, this may be the case if a single family doctor has multiple patients in the system 100, and the family doctor is provided access to the medical image data 138 of their various patients. In such an embodiment, the token can be validated for such a user, and a user interface may be presented for the family doctor to view all associated medical image data 138.

In various embodiments, different types of data stored using the database schema 1900 may be stored in a different physical storage mediums and/or different respective physical locations. For example, various legislative and/or regulatory requirements may require certain types of data to be stored within a certain geographical boundary, encrypted or otherwise secured to a particular security level, and/or stored separate from other types of data. In the illustrated example, patient medical records in the "Patient" dataset 1906 may potentially be stored separately, and physically remotely from the other datasets to comply with such requirements.

Referring again to FIG. 1, in a variant embodiments, the medical imaging data 138 may be acquired by a medical professional that is guided by an interactive application (e.g., provided by the imaging app 112, the medical imaging device 102, and/or the computing device 110). For instance, the interactive application may guide the medical professional to capture particular views of a particular portion of the patient. The interactive application may also generate various other data that is derived from the images as medical imaging data 138. For example, the interactive application may direct the medical professional to perform various measurements on the images and/or automatically derive the measurements from the images.

In a particular example embodiment, the interactive application may provide a guided protocol that helps with acquisition of specific cardiac views so as to automatically perform certain cardiac measurements (e.g., ejection fraction). In this example, once the patient identifier is entered via the new patient interface (as discussed above), the patient may access formatted data that includes optionally images and some of the measurements and an interpretation.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

What is claimed is:

1. A method for initiating creation of a patient-access account on an ultrasound imaging system during an ultrasound imaging examination, the method comprising operating a processor to:
    acquire a set of ultrasound imaging data during the ultrasound imaging examination, the set of ultrasound imaging data being acquired in association with a logged-in medical professional account on the ultrasound imaging system and displayed on an interface operable by the logged-in medical professional;
    display on the interface, after acquiring the set of ultrasound imaging data and prior to completion of the ultrasound imaging examination, a new patient-access account prompt to initiate creation of the patient-access account, the patient-access account being for the patient to access at least a portion of the set of ultrasound imaging data acquired during the ultrasound imaging examination;
    receive, via the new patient-access account prompt, a patient identifier to initiate the creation of the patient-access account on the ultrasound imaging system; and
    use the patient identifier to initiate the creation of the patient-access account.

2. The method of claim 1, wherein the new patient-access account prompt is displayed while the medical professional account remains logged in on the ultrasound imaging system.

3. The method of claim 1, wherein using the patient identifier to initiate the creation of the patient-access account comprises operating the processor to:
    initiate the creation of the patient-access account as a subsidiary account of the medical professional account, the subsidiary account being assigned a lower access level to ultrasound data accessible via the ultrasound imaging system than an access level assigned to the medical professional account.

4. The method of claim 1, wherein after completion of the ultrasound imaging examination, operating the processor to:
    use the patient identifier to request a patient access approval prior to granting access to the at least a portion of the set of ultrasound imaging data acquired during the ultrasound medical imaging examination.

5. The method of claim 1, wherein the patient identifier comprises a contact data and the method further comprises operating the processor to, after the initiation of the creation of the patient-access account during the ultrasound imaging examination, transmit a patient-access account link using the contact data.

6. The method of claim 5, wherein transmitting the patient-access account link comprises operating the processor to transmit a patient-access account completion link that is usable to enable completing the creation of the patient-access account on the ultrasound imaging system.

7. The method of claim 5, wherein transmitting the patient-access account link comprises operating the processor to transmit a patient-access account access link that enables the patient to access the set of ultrasound imaging data acquired during the ultrasound imaging examination.

8. The method of claim 1, further comprising operating the processor to:
    determine whether the patient-access account is associated with the logged-in medical professional account on the ultrasound imaging system; and
    display a new professional association prompt to initiate an account link between the patient-access account and the medical professional account when the patient-access account is not associated with the logged-in medical professional account on the ultrasound imaging system.

9. The method of claim 1, wherein the new patient-access account prompt comprises a new patient-access account interface having a patient identifier field for receiving the patient identifier.

10. A system for initiating creation of a patient-access account on an ultrasound imaging system during an ultrasound imaging examination, the system comprising:
    a storage component operable to store patient account data associated with each user account of one or more user accounts on the ultrasound imaging system;
    a processor operable to:
        acquire a set of ultrasound medical imaging data during the ultrasound imaging examination, the set of ultrasound imaging data being acquired in association with a logged-in medical professional account on the ultrasound imaging system and displayed on an interface operable by the logged-in medical professional;
        display on the interface, after acquiring the set of ultrasound imaging data and prior to completion of the ultrasound imaging examination, a new patient-access account prompt to initiate creation of the patient-access account, the patient-access account being for the patient to access at least a portion of the set of ultrasound imaging data acquired during the ultrasound imaging examination;
        receive, via the new patient-access account prompt, a patient identifier to initiate the creation of the patient-access account on the ultrasound imaging system; and
        use the patient identifier to initiate the creation of the patient-access account.

11. The system of claim 10, wherein the processor is operable to display the new patient-access account prompt while the medical professional account remains logged-in on the ultrasound imaging system.

12. The system of claim 10, wherein the processor is operable to:
    initiate the creation of the patient-access account as a subsidiary account of the medical professional account, the subsidiary account being assigned a lower access level to medical data accessible via the medical imaging system than an access level assigned to the medical professional account.

13. The system of claim 10, wherein after completion of the ultrasound imaging examination, the processor is operable to:
    use the patient identifier to request a patient access approval prior to granting access to the set of ultrasound imaging data acquired during the ultrasound imaging examination.

14. The system of claim 10, wherein the patient identifier comprises a contact data and the processor is operable to, after the initiation of the creation of the patient-access account during the ultrasound imaging examination, transmit a patient account link using the contact data.

15. The system of claim 14, wherein the processor is operable to transmit a patient-access account completion link that is usable to enable completing the creation of the patient-access account on the ultrasound imaging system.

16. The system of claim 14, wherein the processor is operable to transmit a patient-access account access link that enables the patient to access the set of ultrasound imaging data acquired during the ultrasound imaging examination.

17. The system of claim 10, wherein the processor is operable to:
- determine whether the patient-access account is associated with the logged-in medical professional account on the ultrasound imaging system; and
- display a new professional association prompt to initiate an account link between the patient-access account and the medical professional account when the patient-access account is not associated with the logged-in medical professional account on the ultrasound imaging system.

18. The system of claim 10, wherein the new patient-access account prompt comprises a new patient-access account interface having a patient identifier field for receiving the patient identifier.

\* \* \* \* \*